United States Patent
Kajiro et al.

(10) Patent No.: US 9,630,164 B2
(45) Date of Patent: Apr. 25, 2017

(54) POROUS POLYMER METAL COMPLEX, GAS ADSORBENT, AND GAS SEPARATION DEVICE AND GAS STORAGE DEVICE USING SAME

(71) Applicants: NIPPON STEEL & SUMITOMO METAL CORPORATION, Tokyo (JP); Kyoto University, Kyoto-shi, Kyoto (JP)

(72) Inventors: Hiroshi Kajiro, Kimitsu (JP); Koichi Nose, Chiba (JP); Susumu Kitagawa, Kyoto (JP); Ryotaro Matsuda, Kyoto (JP); Hiroshi Sato, Kyoto (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 0 days.

(21) Appl. No.: 14/440,014

(22) PCT Filed: Oct. 31, 2013

(86) PCT No.: PCT/JP2013/079566
§ 371 (c)(1),
(2) Date: Apr. 30, 2015

(87) PCT Pub. No.: WO2014/069574
PCT Pub. Date: May 8, 2014

(65) Prior Publication Data
US 2015/0290618 A1    Oct. 15, 2015

(30) Foreign Application Priority Data

Nov. 2, 2012 (JP) ................................. 2012-242890
Nov. 2, 2012 (JP) ................................. 2012-242928
(Continued)

(51) Int. Cl.
*C07F 1/08* (2006.01)
*B01J 20/26* (2006.01)
(Continued)

(52) U.S. Cl.
CPC ............. *B01J 20/26* (2013.01); *B01D 53/02* (2013.01); *B01J 20/226* (2013.01); *C07C 63/24* (2013.01);
(Continued)

(58) Field of Classification Search
CPC ......... B01J 31/1691; C07F 1/08; F17C 11/00; C08G 79/00; B01D 53/02; C07C 63/24
(Continued)

(56) References Cited

U.S. PATENT DOCUMENTS

2002/0120165 A1    8/2002    Zaworotko et al.

FOREIGN PATENT DOCUMENTS

JP    2000-109493 A    4/2000
JP    2000-202283 A    7/2000
(Continued)

OTHER PUBLICATIONS

An et al., "High and Selective CO2 Uptake in a Cobalt Adeninate Metal-Organic Framework Exhibiting Pyrimidine- and Amino-Decorated Pores", J. Am. Chem. Soc. 2010, 132, pp. 38-39.
(Continued)

*Primary Examiner* — Porfirio Nazario Gonzalez
(74) *Attorney, Agent, or Firm* — Birch, Stewart, Kolasch & Birch, LLP

(57) ABSTRACT

An object of the present invention is to provide a porous polymer metal complex which can be used as a gas adsorbent and contains two or more types of similar ligands. A porous polymer metal complex is provided expressed by $[CuX]_n$ (1) (in the Formula, X represents two or more types of isophthalic acid ions selected from the group consisting of
(Continued)

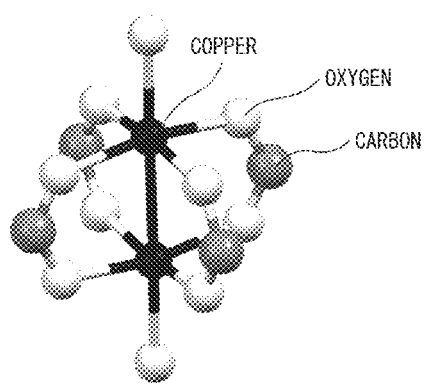

PADDLE-WHEEL STRUCTURE isophthalic acid ions and isophthalic acid ions having a substituent at position 5, at least an amount of one type of X is 5 mol % to 95 mol % of the total number of moles of X, and n represents an assembly number of constituent units expressed by CuX and is not particularly limited).

21 Claims, 7 Drawing Sheets

(30) Foreign Application Priority Data

Nov. 2, 2012 (JP) .................. 2012-242936
Nov. 2, 2012 (JP) .................. 2012-243061

(51) Int. Cl.
| | |
|---|---|
| *B01D 53/02* | (2006.01) |
| *C08G 79/00* | (2006.01) |
| *C07C 63/24* | (2006.01) |
| *F17C 11/00* | (2006.01) |
| *B01J 20/22* | (2006.01) |
| *B01D 53/047* | (2006.01) |

(52) U.S. Cl.
CPC .............. *C07F 1/08* (2013.01); *C08G 79/00* (2013.01); *F17C 11/00* (2013.01); *B01D 53/047* (2013.01); *B01D 2253/1122* (2013.01); *B01D 2253/202* (2013.01)

(58) Field of Classification Search
USPC ........................................... 556/115
See application file for complete search history.

(56) References Cited

FOREIGN PATENT DOCUMENTS

| | | |
|---|---|---|
| JP | 2008-266269 A | 11/2008 |
| JP | 2011-37794 A | 2/2011 |
| JP | 2011-68631 A | 4/2011 |
| JP | 2012-180322 A | 9/2012 |
| JP | 2012-228667 A | 11/2012 |

OTHER PUBLICATIONS

Biffinger et al., "The Polar Hydrophobicity of Fluorinated Compounds", ChemBioChem, 2004, 5, pp. 622-627.
Chen et al., "Rationally Designed Micropores within a Metal-Organic Framework for Selective Sorption of Gas Molecules", Inorganic Chemistry, vol. 46, No. 4, 2007, pp. 1233-1236.
D'Alessandro et al., "Carbon Dioxide Capture: Prospects for New Materials", Angew. Chem. Int. Ed. 2010, 49, pp. 2-27.
Deng et al., "Multiple Functional groups of Varying Ratios in Metal-Organic Frameworks", vol. 327, Science, Feb. 12, 2010, pp. 846-850.
Devic et al., "Functionalization in Flexible Porous Solids: Effects on the Pore Opening and the Host-Guest Interactions", J. Am. Chem. Soc. 2010, 132, pp. 1127-1136.
Fischer et al., "Functionalized Coordination Space in Metal Organic Frameworks", Angew. Chem. Int. Ed. 2008, 47, pp. 2-7.
Fukushima et al., "Solid Solutions of Soft Porous Coordination Polymers: Fine-Tuning of Gas Adsorption Properties", Wiley InterScience, Angew. Chem. 2010, 122, pp. 4930-4934.
Galli et al., "Polymorphic Coordination Networks Responsive to CO2, Moisture, and Thermal Stimuli: Porous Cobalt(II) and Zinc(II) Fluoropyrimidinolates", Chem. Eur. J. 2008, 14, pp. pp. 9890-9901.
International Search Report, mailed Dec. 24, 2013, issued in PCT/JP2013/079566.
Kitagawa et al., "Functional Micropore Chemistry of Crystalline Metal Complex-Assembled Compounds", The Chemical Society of Japan, Bull. Chem. Soc. Jpn., 71, pp. 1739-1753 (1998).
Kleist et al., "Mixed-Linker Metal-Organic Frameworks as Catalysts for the Synthesis of Propylene Carbonate from Propylene Oxide and CO2", Wiley InterScience, Eur. J. Inorg. Chem. 2009, pp. 3552-3561.
Koh et al., "A Porous Coordination Copolymer with over 5000 m²/g BET Surface Area", J. Am. Chem. Soc. 2009, 131, pp. 4184-4185.
Matsuda et al., "Highly controlled acetylene accommodation in a metal-organic microporous material", Nature, vol. 436, Jul. 14, 2005, pp. 238-241.
Moon et al., "Porous Metal-Organic Framework with Coordinatively Unsaturated MnII Sites:Sorption Properties for Various Gases", Inorganic Chemistry, vol. 45, No. 21, 2006, pp. 8672-8676.
Nagai, CMC Publishing Co., Ltd., "Gas Separation, Permeation and Barrier Membranes", 2007, 210-211.
Pan et al., "Microporous Metal Organic Materials: Promising Candidates as Sorbents for Hydrogen Storage", J. Am. Chem. Soc. 2004, 126, pp. 1308-1309.
Park et al., "Nonlinear Properties in Coordination Copolymers Derived from Randomly Mixed Ligands", ACS Publications, Crystal Growth and Design, 2011, 2059.
Perry et al., "Sextuplet phenyl embrace in a metal-organic Kagomé lattice", Chem. Commun., 2004, pp. 2534-2535.
Susumu Kitagawa, "Cluster type Metal Complex", Kodansha Scientific Ltd., 2001, pp. 214-218.
Wen et al., "Hydrothermal syntheses, crystal structures and characterizations of three new copper coordination polymers", Available online at www.sciencedirect.com, Inorganica Chimica Acta 358, (2005), pp. 3347-3354.
Written Opinion of the International Searching Authority, mailed Dec. 24, 2013, issued in PCT/JP2013/079566.
Yamatsugu et al., "Identification of Potent, Selective Protein Kinase C Inhibitors Based on a Phorbol Skeleton", Chem. Asian J. 2006, 1, pp. 314-321.
Yang et al., "Crystallographic Observation of Dynamic Gas Adsorption Sites and Thermal Expansion in a Breathable Fluorous Metal-Organic Framework**", Wiley InterScience, Angew. Chem. Int. Ed. 2009, 48, pp. 2500-2505.
Yang et al., "Fluorous Metal-Organic Frameworks for High-Density Gas Adsorption", J. Am. Chem. Soc. 2007, 129, pp. 15454-15455.
Zhang et al., "A Highly Connected Porous Coordination Polymer with Unusual Channel Structure and Sorption Properties**", Wiley InterScience, Angewandte Chemie, Int. Ed. 2009, 48, pp. 5287-5290.
Eubank et al., "The Next Chapter in MOF Pillaring Strategies: Trigonal Heterofunctional Ligands to Access Targeted High-Connected Three Dimensional Nets, Isoreticular Platforms", Journal of the American Chemical Society, vol. 133, No. 44, Jun. 15, 2011, pp. 17532-17535.
Extended European Search Report for corresponding European Application No. 15851100.1, mailed Jun. 24, 2016.

PADDLE-WHEEL STRUCTURE

POROUS POLYMER METAL COMPLEX, GAS ADSORBENT, AND GAS SEPARATION DEVICE AND GAS STORAGE DEVICE USING SAME

TECHNICAL FIELD OF THE INVENTION

The present invention relates to a porous polymer metal complex, a gas adsorbent, and a gas separation device and a gas storage device using same.

PRIOR ART

A gas adsorbent has a property of being capable of storing a large amount of gas at a low pressure compared to pressurization storage or liquefaction storage. Therefore, in recent years, the development of a gas storage device or a gas separation device using the gas adsorbent has been actively progressing. As the gas adsorbent, activated carbon and zeolite are known. Recently, a method of occluding gas by a porous polymer metal complex has also been proposed (refer to Patent Document 1 and Non-Patent Document 1).

A porous polymer metal complex is a crystalline solid obtained from metal ions and organic ligands and has a possibility of exhibiting various gas adsorption properties due to the combination of various types of metal ions and organic ligands and the diversity of skeleton structures. However, the gas adsorbent that has been proposed hitherto is not sufficiently satisfactory in terms of gas adsorption amount, workability, and the like, and thus the development of a gas adsorbent having better properties is desirable.

It is known that an inorganic adsorbent such as zeolite and activated carbon has enhanced gas adsorption properties by adding metal salts thereto or performing a chemical conversion treatment thereon. The porous polymer metal complex itself contains metal ions. Therefore, adding a different type of metal salts or performing the chemical conversion treatment may cause the decomposition of the material. In this regard, little is known about a method of adding metal salts or performing a chemical conversion treatment on a porous polymer metal complex.

In addition, in the case of an inorganic material, there is a material or a technique called a solid solution, in which a noble material is created by continuously changing the mixing ratio of a plurality of types of raw materials. Here, the solid solution is generally known as a material in which similar raw materials A and B are present at positions where they can crystallographically substitute for each other in the material. Particularly, it is worth focusing on a case in which an enhancement effect of obtaining better properties when the raw materials A and B are mixed with each other than when the raw materials A and B are separately used is recognized.

Here, when the enhancement effect is described by exemplifying gas adsorption and separation, for example, it is defined that a material obtained when the raw materials A and B are mixed with each other has a larger gas storage amount or further enhanced gas separation properties than when the raw materials A and B are separately used.

By applying this concept to the porous polymer metal complex, when a plurality of types of similar ligands can be mixed with each other for use and the enhancement effect is further obtained, an excellent material can be created. An example of synthesizing a non-solid-solution type porous polymer metal complex by mixing a plurality of different ligands at a specific mixing ratio for use is relatively well known (Non-Patent Documents 2 and 3). However, a practical example in which a solid solution type porous polymer metal complex for use at an arbitrary mixing ratio is synthesized by mixing a plurality of types of similar ligands is extremely rare (Non-Patent Documents 4 to 6). This is because a porous polymer metal complex is formed based on the principle that a crystal automatically produces network bonds in a solution due to the interaction between metals and ligands, called self-assembly. Specifically, this is caused due to the principle that even when a plurality of types of similar ligands are used as raw materials, only one type of ligand selectively forms a porous polymer metal complex, only one type of ligand is included in the obtained porous polymer metal complex.

Furthermore, even in Non-Patent Documents 4 to 6, the obtained properties are simply the sum of effects of raw materials, and an example in which the enhancement effect is obtained by using a mixture of a plurality of types of similar ligands to form a porous polymer metal complex is rare.

In addition, in Non-Patent Document 7, there is a description in which, when a solid solution is synthesized by two types of ligands and the ligands are mixed at an appropriate ratio, the maximum specific surface area (gas adsorption amount) is obtained. However, it is described that, in a solid solution in which one ligand (Me4BPDC) is present in a high proportion, the network structure becomes a so-called interpenetration structure. It is known that in the interpenetration structure, voids of one lattice are buried by another penetrating lattice, and the substantial voids are significantly reduced in size. That is, in this non-patent document, in the solid solution in which one ligand (Me4BPDC) has a high use rate, the specific surface area (gas adsorption amount) is reduced by the interpenetration. Therefore, although it can be seen from the graph that the enhancement effect is obtained, actually, this enhancement effect is superficial. That is, the enhancement effect is not caused by an increase in the adsorption amount due to the solid solution formation but is merely a relative enhancement effect caused by a reduction in the adsorption amount on a part of the solid solution.

That is, when a porous polymer metal complex is synthesized using a plurality of types of similar ligands and an enhancement effect is obtained, there is a possibility that the development of an excellent gas adsorbent may be achieved. However, a method to realize such a development is not known.

In addition, carbon dioxide gas is a cause of global warming. An adsorbent for storing a large amount of this gas, particularly, for selectively separating and storing only carbon dioxide gas is very important. In general, in order to separate and store gas, a so-called porous body having a large number of pores is used as an adsorbent. However, most adsorbents for trapping carbon dioxide trap gases other than carbon dioxide, for example, nitrogen, oxygen, and the like. Particularly, at a low temperature, the interaction between pores and gases becomes strong, and in principle, many porous bodies trap various types of gases. Therefore, a method to manufacture an adsorbent which selectively traps only carbon dioxide in a wide temperature range is unknown (Non-Patent Documents 8 to 11).

It is known that in a porous polymer metal complex, various substituents can be introduced as organic ligands and various properties can be exhibited by the functional groups (Non-Patent Documents 12 and 13). However, since this porous polymer metal complex is a noble material, practically, it is unclear what property is exhibited when a certain functional group is introduced thereto. In theory, it is clear that when porosity is increased as much as possible, the amount of gas that can be stored therein increases. However, an increase in porosity means that the material may become fragile. In practice, based on the fact that in an initial stage of the study of the porous polymer metal complex, a material capable of maintaining its pores without causing the collapse of the structure is overwhelmingly rare, it can be seen that it is difficult to increase porosity while maintaining structure (Non-Patent Document 14). An established opinion regarding the balancing between the enhancement of porosity and structural stabilization does not exist.

In addition, it can be imagined that a material is stabilized by introducing as many rigid molecules as possible. In practice, a porous polymer metal complex in which a phenyl group of which molecules are large and rigid is introduced in pores is also reported. However, gas adsorption properties and thermal stability are unclear (Non-Patent Document 15). In addition, in a case where large molecules are simply introduced, it can be easily expected that the pore capacity is reduced, the gas adsorption amount is reduced, and thus there is a problem in designing an adsorbent.

As described above, there have been attempts to control adsorption properties of a porous polymer metal complex using functional groups. For example, a porous polymer metal complex which absorbs acetylene at a high density by introducing a carboxyl group which selectively interacts with acetylene is known (Non-Patent Document 16).

It is known that fluorine atoms have unique interactions (Non-Patent Document 17), and particularly, polyfluoroalkyl has a strong affinity to carbon dioxide or oxygen. This phenomenon is called liquid respiration (Non-Patent Document 18). When the special properties of fluorine atoms are introduced to a porous polymer metal complex, it is thought that a special gas adsorption and separation material can be created. However, the interaction of fluorine is very weak compared to the interaction between acetylene and a carboxyl group described above. In addition, although there is a report that a porous polymer metal complex in which fluorine atoms are introduced has an effect on adsorption of carbon dioxide or hydrogen, it cannot be said that the effect is positively significant. Furthermore, the effect on other types of gases is unclear (Non-Patent Documents 19 to 22), and a method to introduce fluorine atoms to a porous polymer metal complex to obtain a significant effect is unknown.

PRIOR ART DOCUMENT

Patent Document

Patent Document 1: Japanese Unexamined Patent Application, First Publication No. 2000-109493

Non-Patent Document

Non-Patent Document 1: Susumu Kitagawa, Cluster type Metal Complex, Kodansha Scientific Ltd. 2001, p. 214 to 218
Non-Patent Document 2: Matzger, J. AM. CHEM. SOC. 2009, 131, 4184-4185
Non-Patent Document 3: Chen, Angew. Chem. Int. Ed. 2009, 48, 5287-5290
Non-Patent Document 4: Yaghi, Science 327, 846 (2010)
Non-Patent Document 5: Fukushima, Angewandte Chemie, 2010, Volume 122, Issue 28, page 4930
Non-Patent Document 6: Baiker, Eur. J. Inorg. Chem. 2009, 3552
Non-Patent Document 7: Matzger, Crystal Growth and Des., 2011, 2059
Non-Patent Document 8: Long et al., Angew. Chem. Int. Ed. 2010, 49, 2-27
Non-Patent Document 9: Suh et al., Inorganic Chemistry, Vol. 45 , No. 21, 2006
Non-Patent Document 10: Zhou et al., Inorganic Chemistry, Vol. 46, No. 4, 2007 1233
Non-Patent Document 11: Rosi et al., J. AM. CHEM. SOC. 2010, 132, 38-39
Non-Patent Document 12: Fischer et al., Angew. Chem. Int. Ed. Engl., 2008,47, 2
Non-Patent Document 13: Devic et al., J. AM. CHEM. SOC. 2010, 132, 1127-1136
Non-Patent Document 14: Kitagawa et al., Bull. Chem. Soc. Jpn., 71 (1998) 1739
Non-Patent Document 15: Zaworotko et al., Chem. Commun., 2004, 2534-2535
Non-Patent Document 16: Kitagawa et al., Nature (2005) 436, 238
Non-Patent Document 17: DiMagno et al., ChemBioChem 2004, 5, 622
Non-Patent Document 18: Nagai et al., CMC Publishing Co., Ltd., Gas Separation, Permeation and Barrier Membranes, 210-211
Non-Patent Document 19: Navarro et al., Chem. Eur. J. 2008, 14, 9890-9901
Non-Patent Document 20: Omary et al., J. Am. Chem. Soc., 2007, 129, 15454
Non-Patent Document 21: Omary et al., Angew. Chem. Int. Ed. 2009, 48, 2500
Non-Patent Document 22: Li et al., J. Am. Chem. Soc., 2004, 126, 1308

DISCLOSURE OF THE INVENTION

Problems to be Solved by the Invention

The present invention provides a porous polymer metal complex and a gas adsorbent having excellent properties using same. In addition, an object of the present invention is to also provide a gas storage device and a gas separation device configured to store the gas adsorbent having the properties therein.

Means for Solving the Problem

The present inventors intensively and repeatedly studied to solve the above-described problems, and as a result, found that when two or more types selected from the group consisting of isophthalic acid ions and isophthalic acid ions having a substituent at position 5 and copper ions are selected, by reactions therebetween, a porous polymer metal complex having a so-called Kagome structure is obtained. Moreover, the porous polymer metal complex also contains two or more types of ligands used as raw materials (a solid solution type porous polymer metal complex is formed), is characterized by controlling its properties for gas adsorption and separation properties, and has an enhancement effect, such that the present invention is completed.

That is, a first porous polymer metal complex of the present invention is a porous polymer metal complex which has a basic skeleton of a Kagome structure and contains an isophthalic acid or two or more types of isophthalic acid ligands having a substituent at position 5.

In addition, the present inventors found that a porous polymer metal complex having a so-called Kagome structure which is obtained by reactions between an isophthalic acid derivative having a substituted amino group at position 5 and copper ions selectively traps carbon dioxide in a wide temperature range and completed the present invention.

That is, a second porous polymer metal complex of the present invention is a porous polymer metal complex which has a basic skeleton of a Kagome structure and contains an isophthalic acid derivative ligand having a substituted amino group at position 5.

In addition, the inventors found that a porous polymer metal complex having a so-called Kagome structure which is synthesized from an isophthalic acid derivative having a branched alkyl group at position 5 or a branched alkoxy group at position 5 traps a large amount of various gases and completed the present invention.

That is, the present invention is related to a porous polymer metal complex which has a basic skeleton of a Kagome structure and contains an isophthalic acid ligand having a branched alkyl group at position 5 or an isophthalic acid ligand having a branched alkoxy group at position 5, and usage of the present material as the gas adsorbent, and a gas storage device and a gas separation device which accommodate the gas adsorbent therein.

Furthermore, the inventors found that a porous polymer metal complex obtained by reactions between an isophthalic acid derivative in which position 5 is substituted by a perfluoroalkyl group containing 3 to 21 fluorine atoms or by a perfluoroalkoxy group containing 3 to 21 fluorine atoms and copper ions traps a large amount of various gases and exhibits a specific adsorption phenomenon depending on the gas type, and completed the present invention.

That is, the present invention is related to a porous polymer metal complex which has a basic skeleton of a Kagome structure and contains an isophthalic acid derivative in which position 5 is substituted by a perfluoroalkyl group containing 3 to 21 fluorine atoms or by a perfluoroalkoxy group containing 3 to 21 fluorine atoms and copper ions, and usage of the present material as the gas adsorbent and a gas storage device and a gas separation device which accommodate the gas adsorbent therein.

Specifically, in order to accomplish the object, the present invention provides a porous polymer metal complex, a gas adsorbent, and a gas separation device and a gas storage device using the same as follows.

(1) A porous polymer metal complex expressed by the following Formula:

$$[CuX]_n \qquad (1)$$

(in the Formula, X represents two or more types of isophthalic acid ions selected from the group consisting of isophthalic acid ions and isophthalic acid ions having a substituent at position 5, at least an amount of one type of X is 5 mol % to 95 mol % of the total number of moles of X, and n represents an assembly number of constituent units expressed by CuX and is not particularly limited).

(2) The porous polymer metal complex described in (1), expressed by the following Formula:

$$[CuX_{1-m}Y_m]_n \qquad (2)$$

(in the Formula, each of X and Y represents isophthalic acid ions or isophthalic acid ions having a substituent at position 5, X and Y are different from each other, $0.05 \leq m \leq 0.95$ is satisfied, and n represents an assembly number of constituent units expressed by $CuX_{1-m}Y_m$ and is not particularly limited).

(3) The porous polymer metal complex described in (1) or (2), in which the porous polymer metal complex has a paddle-wheel structure having vertically coordinated two units in which a copper ion is coordinated to four carboxyl groups, the paddle-wheel structure is connected by isophthalic acid derivatives to form a Kagome structure constituted by six-membered rings and three-membered rings, and the Kagome structure has a stacked crystal structure.

(4) The porous polymer metal complex described in (1) to (3), in which X in Formula (1) or X or Y in Formula (2) represents isophthalic acid ions having a substituent at position 5, and the substituent at position 5 is a functional group selected from the group consisting of a methyl group, an ethyl group, a methoxy group, an ethoxy group, a tert-butyl group, a benzyloxy group, a nitro group, an azido group, a carboxyl group, an amino group, and a hydroxyl group.

(5) The porous polymer metal complex described in (2) or (3), in which X and Y in Formula (2) represent isophthalic acid ions having a substituent at position 5, the substituent at position 5 of X is a functional group selected from the group consisting of a methoxy group, a tert-butyl group, and a nitro group, the substituent at position 5 of Y is a functional group selected from the group consisting of a methyl group, an ethyl group, a methoxy group, an ethoxy group, a tert-butyl group, a benzyloxy group, a nitro group, an azido group, a carboxyl group, an amino group, and a hydroxyl group, and X and Y are different from each other.

(6) A gas adsorbent including the porous polymer metal complex described in (1) to (5).

(7) A gas separation device which uses the gas adsorbent described in (6).

(8) A gas storage device which uses the gas adsorbent described in (6).

(9) A porous polymer metal complex expressed by the following Formula (21):

$$[CuX]_n \qquad (21)$$

(in the Formula, X represents isophthalic acid ions having a substituted amino group at position 5, and n represents an assembly number of constituent units expressed by CuX and is not particularly limited).

(10) The porous polymer metal complex described in (9), in which the porous polymer metal complex has a paddle-wheel structure having vertically coordinated two units in which a copper ion is coordinated to four carboxyl groups, the paddle-wheel structure is connected by isophthalic acid derivatives to form a Kagome structure constituted by six-membered rings and three-membered rings, and the Kagome structure has a stacked crystal structure.

(11) The porous polymer metal complex described in (9) or (10), in which the substituted amino group is an amino group substituted with an alkyl group or an aryl group.

(12) The porous polymer metal complex described in (9) to (11), in which the substituted amino group is a functional group selected from the group consisting of a methylamino group, a dimethylamino group, an ethylamino group, and a diethylamino group.

(13) A porous polymer metal complex expressed by the following Formula (24):

$$[CuX]_n \qquad (24)$$

(in the Formula, X represents two or more types of isophthalic acid ions selected from the group consisting of isophthalic acid ions and isophthalic acid ions having a substituent at position 5, an amount of the isophthalic acid ions having a substituted amino group at position 5 is 5 mol % or more with respect to the total number of moles of X, and n represents an assembly number of constituent units expressed by CuX and is not particularly limited).

(14) The porous polymer metal complex described in (13), in which X in Formula (24) represents two or more types of ions selected from the group consisting of isophthalic acid ions, isophthalic acid ions having an alkyl group at position 5, isophthalic acid ions having an alkoxy group at position 5, isophthalic acid ions having an amino group, and isophthalic acid ions having a substituted amino group, and an amount of the isophthalic acid ions having a substituted amino group at position 5 is 5 mol % or more with respect to the total number of moles of X.

(15) An adsorbent including the porous polymer metal complex described in (9) to (14).

(16) A gas separation device which uses the adsorbent described in (15).

(17) A gas storage device which uses the adsorbent described in (15).

(18) A porous polymer metal complex expressed by Formula (31):

$$[CuX]_n \qquad (31)$$

(in the Formula, X represents isophthalic acid ions having a branched alkyl group at position 5 or isophthalic acid ions having a branched alkoxy group at position 5, and n represents an assembly number of constituent units expressed by CuX and is not particularly limited).

(19) The porous polymer metal complex described in (18), in which the porous polymer metal complex has a paddle-wheel structure having vertically coordinated two units in which a copper ion is coordinated to four carboxyl groups, the paddle-wheel structure is connected by isophthalic acid derivatives to form a Kagome structure constituted by six-membered rings and three-membered rings, and the Kagome structure has a stacked crystal structure.

(20) The porous polymer metal complex described in (18) or (19), in which the branched alkyl group is a functional group selected from the group consisting of an isopropyl group, a tert-butyl group, and an isobutyl group, and the branched alkoxy group is a functional group selected from the group consisting of an isopropyloxy group, a tert-butyloxy group, and an isobutyloxy group.

(21) A porous polymer metal complex expressed by Formula (34):

$$[CuX]_n \qquad (34)$$

(in the Formula, X represents ions of two or more types of isophthalic acids selected from isophthalic acid ions and isophthalic acid ions having a substituent at position 5, an amount of isophthalic acid ions having a branched alkyl group or a branched alkoxy group at position 5 is 5 mol % or more with respect to the total number of moles of X, and n represents an assembly number of constituent units expressed by CuX and is not particularly limited).

(22) The porous polymer metal complex described in (21), in which X in Formula (34) represents ions of two or more types of isophthalic acids selected from the group consisting of isophthalic acid ions, isophthalic acid ions having an alkyl group at position 5, isophthalic acid ions having an alkoxy group at position 5, isophthalic acid ions having a unsubstituted or substituted amino group at position 5, and an amount of isophthalic acid ions having a branched alkyl group at position 5 or isophthalic acid ions having a branched alkoxy group at position 5 is 5 mol % or more with respect to the total number of moles of X.

(23) An adsorbent including the porous polymer metal complex described in (18) to (22).

(24) A gas separation device which uses the adsorbent described in (23).

(25) A gas storage device which uses the adsorbent described in (23).

(26) A porous polymer metal complex expressed by the following Formula (41):

$$[CuX]_n \qquad (41)$$

(in the Formula, X represents isophthalic acid ions in which position 5 is substituted by a perfluoroalkyl group containing 3 to 21 fluorine atoms or isophthalic acid ions in which position 5 is substituted by a perfluoroalkoxy group containing 3 to 21 fluorine atoms, and n represents an assembly number of constituent units expressed by CuX and is not particularly limited).

(27) A porous polymer metal complex expressed by the following Formula (44):

$$[CuX]_n \qquad (44)$$

(in the Formula, X includes at least one type of non-fluorinated isophthalic acid ions selected from the group consisting of isophthalic acid ions in which position 5 is substituted by an alkyl group having 1 to 10 carbon atoms, isophthalic acid ions in which position 5 is substituted by an alkoxy group having 1 to 10 carbon atoms, and isophthalic acid ions, and at least one type of fluorinated phthalic acid derivative ions selected from the group consisting of isophthalic acid ions in which position 5 is substituted by a perfluoroalkyl group containing 3 to 21 fluorine atoms and isophthalic acid derivative ions in which position 5 is substituted by a perfluoroalkoxy group containing 3 to 21 fluorine atoms, an amount of the fluorinated isophthalic acid ions is 5 mol % or more with respect to the total number of moles of X, and n represents an assembly number of constituent units expressed by CuX and is not particularly limited).

(28) The porous polymer metal complex described in (26) or (27), in which the porous polymer metal complex has a paddle-wheel structure having vertically coordinated two units in which a copper ion is coordinated to four carboxyl groups, the paddle-wheel structure is connected by isophthalic acid derivatives to form a Kagome structure constituted by six-membered rings and three-membered rings, and the Kagome structure has a stacked crystal structure.

(29) The porous polymer metal complex described in (26) to (28), in which X represents isophthalic acid ions in which position 5 is substituted by a perfluoroalkyl group or a perfluoroalkoxy group selected from n-$C_3F_7$, n-$C_4F_9$, n-$C_5F_{11}$, n-$C_6F_{13}$, n-$C_7F_{15}$, n-$C_8F_{16}$, O-n-$C_3F_7$, O-n-$C_4F_9$, —O-n-$C_5F_{11}$, O-n-$C_6F_{13}$, O-n-$C_7F_{15}$, and O-n-$C_8F_{16}$ or ions containing the ions thereof.

(30) A gas adsorbent including: the porous polymer metal complex described in (26) to (29).

(31) A gas separation device which uses the gas adsorbent described in (30).

(32) A gas separation device which uses the gas adsorbent described in (30).

Effects of the Invention

The porous polymer metal complex of the present invention can occlude and discharge a large amount of gas and can selectively trap gas. In addition, it is possible to produce a gas storage device and gas separation device which accommodates a gas occlusion material containing the porous polymer metal complex of the present invention therein, and a vehicle in which the gas storage device is mounted.

The porous polymer metal complex of the present invention is a porous polymer metal complex having a so-called Kagome structure by reactions between two or more types selected from the group consisting of isophthalic acid ions and isophthalic acid ions having a substituent at position 5 and copper ions and also contains two or more types of ligands used as the raw material, thereby controlling its properties for gas adsorption and separation properties and exhibiting an enhancement effect.

When the porous polymer metal complex of the present invention is used as, for example, a pressure swing adsorption type (PSA type) gas separation device, it is possible to perform efficient gas separation. In addition, time for a pressure change can be shortened, which contributes to energy savings. Moreover, this also contributes to a reduction in the size of the gas separation device. Therefore, when a high-purity gas is sold as a product, cost competitiveness can be increased as a matter of course. Even in a case where a high-purity gas is used at a factory of own company, cost for a facility which needs the high-purity gas can be reduced. As a result, there is an effect of reducing production cost of the final product.

As another use of the porous polymer metal complex of the present invention, there is a gas storage device. In a case where the gas adsorbent of the present invention is applied to the gas storage device (commercial gas tanks, household gas tanks, vehicle fuel tanks, and the like), it is possible to dramatically reduce pressure during transportation or preservation. As an effect caused by the reduction in gas pressure during transportation or preservation, first, there is an increase in the degree of shape flexibility. In a gas storage device according to the related art, when the pressure is not maintained during preservation, a large gas adsorption amount cannot be maintained. However, in the gas storage device of the present invention, even when the pressure is reduced, a sufficient gas adsorption amount can be maintained. Therefore, the pressure resistance of the container can be reduced, and thus the shape of the gas storage device can be designed with a certain degree of flexibility. This effect is extremely important in a case where the gas storage device of the present invention is used as, for example, the vehicle fuel gas tank of a vehicle or the like. In a case where the gas storage device of the present invention is used as a fuel tank, as described above, restrictions on pressure resistance can be loosened, and thus the shape thereof can be designed with a certain degree of flexibility. Specifically, the shape of the gas storage device can be controlled to fit in the shape of the wheel or seat of a vehicle. As a result, various practical benefits such as a reduction in the size of the vehicle, securing luggage space, and an increase in fuel efficiency due to a reduction in the weight of the vehicle can be obtained.

Regarding container shapes, container materials, gas valve types, and the like in a case of the application to the gas separation device or the gas storage device, particularly special devices need not be used, and those used in the gas separation device or the gas storage device may be used. However, improvements in various devices are not excluded, and even when any device is used, the device is included in the technical scope of the present invention as long as the porous polymer metal complex of the present invention is used.

BRIEF DESCRIPTION OF THE DRAWINGS

In FIG. 7, hydrogen atoms are omitted, copper ions are indicated by black, carbon atoms are indicated by gray, oxygen is indicated by white, and nitrogen is indicated by dark gray.

In FIG. 11, hydrogen atoms and fluorine atoms are omitted, copper ions are indicated by black, carbon atoms are indicated by gray, and oxygen is indicated by white.

EMBODIMENTS OF THE INVENTION

Hereinafter, a porous polymer metal complex, a gas adsorbent, a gas separation device, and a gas storage device of the present invention will be sequentially described in detail.

First, the porous polymer metal complex of the present invention will be described.

Figure 1:
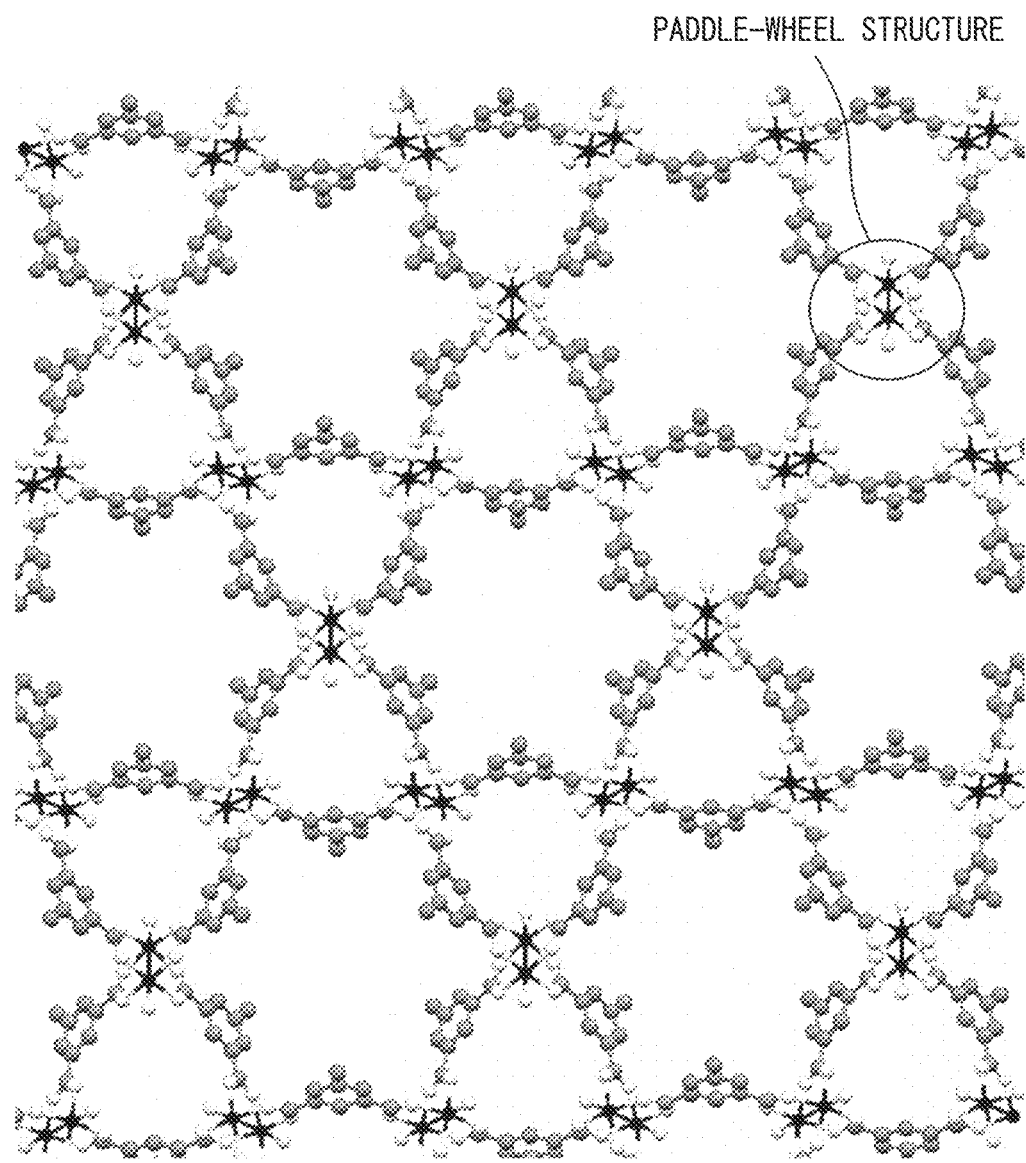
FIG. 1 illustrates the crystal structure (Kagome structure) of an example of a porous polymer metal complex of the present invention, in which hydrogen atoms are omitted, copper ions are indicated by black, carbon atoms are indicated by gray, and oxygen is indicated by white.

(1) Regarding a first porous polymer metal complex, the first porous polymer metal complex of the present invention is a compound that is expressed by the following Formula (1) and has a so-called Kagome structure illustrated in FIG. 1.

(in the Formula, X is two or more types of isophthalic acid ions selected from the group consisting of isophthalic acid ions and isophthalic acid ions having a substituent at position 5, and at least one type thereof occupies 5 mol % to 95 mol % of the total number of moles of X. n represents the assembly number of constituent units expressed by CuX and is not particularly limited.)

The Kagome type porous polymer metal complex of the present invention has, as illustrated in FIG. 1, a network structure (Kagome structure) formed by a combination of large hexagons and small triangles formed with a paddle-wheel structure as the apex. Here, the skeleton of isophthalic acid itself forms the network structure, and the substituent at position 5 itself does not participate in the network formation.

More specifically, the porous polymer metal complex of the present invention has a so-called paddle-wheel structure having vertically coordinated two units in which a copper ion are coordinated to four carboxyl groups (FIG. 2), and the paddle-wheels are connected by isophthalic acid derivatives. In this figure, four oxygen atoms of the carboxylic acids are coordinated to a single copper ion included in the paddle-wheel structure.

Figure 2:
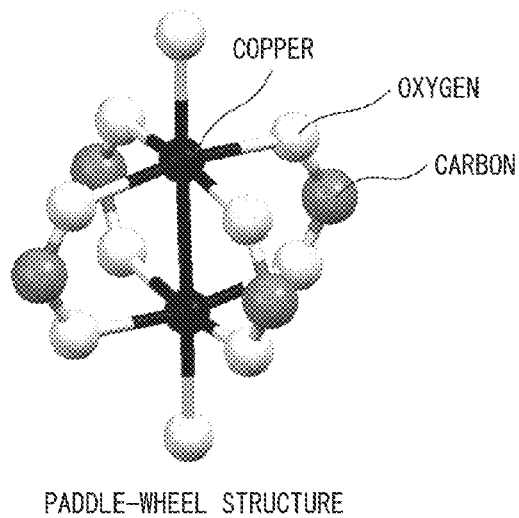
FIG. 2 is a unit structure of the crystal structure of the porous polymer metal complex illustrated in FIG. 1, and illustrates a so-called paddle-wheel structure having vertically coordinated two units in which a copper ion is coordinated to four carboxyl groups.

FIG. 2 illustrates an enlarged view of the so-called paddle-wheel structure having vertically coordinated two units in which a copper ion is coordinated to four carboxyl groups are vertically coordinated. The paddle wheels are connected by the isophthalic acid derivatives such that the Kagome structure constituted by six-membered rings and three-membered rings is formed as illustrated in FIG. 1.

The first porous polymer metal complex of the present invention has a structure in which the so-called Kagome structures formed from copper ions and an isophthalic acid having hydrogen or a substituent at position 5 are stacked. The key factor here is the topology of the network, and an individual bond angle is not always the same as the bond angle in the figure because this compound has flexibility. In addition, regarding the stacked form, two-dimensional Kagome networks are stacked only by weak interactions such as hydrogen bonds and van der Waals forces, and thus there is a possibility that the stacked state may be out of alignment. However, this is also regarded as the same compound having the same function.

Here, X is isophthalic acid ions or isophthalic acid ions having a substituent at position 5. The functional group of isophthalic acid at position 5 is a functional group selected from hydrogen atoms, halogen atoms, a substituted or unsubstituted alkyl group, a substituted or unsubstituted alkoxy group, a substituted or unsubstituted aryl group, an aralkyl group, a substituted or unsubstituted amino group, a nitro group, an amide group, a formyl group, a carbonyl group, an ester group, an azido group, a carboxyl group, a sulfo group, a hydroxyl group, and the like.

As the alkyl group, an alkyl group having 1 to 12, particularly, 1 to 6 carbon atoms such as a methyl group and an ethyl group is preferable. As the substituent of the substituted alkyl group, a hydroxy group, an amino group, and the like may be employed.

As the alkoxy group, an alkoxy group having 1 to 12 carbon atoms, particularly 1 to 6 carbon atoms is preferable, and a methoxy group, an ethoxy group, and a benzyloxy group are particularly preferable. As the substituent of the substituted alkoxy group, a hydroxy group, an amino group, a dimethylamino group, and the like may be employed.

As the aryl group, a phenyl group and a para-hydroxyphenyl group are preferable. As the substituted aryl group, a para-hydroxyphenyl group, a para-dimethylaminophenyl group, and the like may be employed.

As the aralkyl group, a benzyl group, and a phenyl group in which any one or a plurality of o-, m-, and p-positions are substituted by a methyl group and/or an ethyl group are preferable.

As the unsubstituted or substituted amino group, an amino group, a methylamino group, a dimethylamino group, an ethylamino group, a diethylamino group, a phenylamino group, a diphenylamino group, and the like are preferable.

A preferable embodiment of the first porous polymer metal complex of the present invention is a porous polymer metal complex which contains an isophthalic acid ligand having a branched alkyl group at position 5. The porous polymer metal complex has an effect of enabling adsorption of a large amount of various gases.

As an isophthalic acid having a branched alkyl group at position 5, 5-isopropylisophthalic acid, 5-isobutylisophthalic acid, 5-tert-butylisophthalic acid, 5-(2-pentyl)isophthalic acid, 5-(3-pentyl)isophthalic acid, 5-(2-hexyl)isophthalic acid, 5-(3-hexyl)isophthalic acid, 5-isopropyloxyisophthalic acid, 5-isobutyloxyisophthalic acid, 5-tert-butyloxyisophthalic acid, 5-(2-pentyl)oxyisophthalic acid, 5-(3-pentyl)oxyisophthalic acid, 5-(2-hexyl)oxyisophthalic acid, and 5-(3-hexyl)oxyisophthalic acid may be exemplified. A branched alkyl group having 3 or 4 carbon atoms is preferably used, and in terms of a large gas adsorption amount, 5-isopropylisophthalic acid, 5-isobutylisophthalic acid, 5-tert-butylisophthalic acid, 5-isopropyloxyisophthalic acid, 5-isobutyloxyisophthalic acid, and 5-tert-butyloxyisophthalic acid are preferable.

As in the above exemplification, the alkyl group preferably has a branched structure, and the branched structure may be a branched structure having secondary carbon atoms such as an isobutyl group or a branched structure having tertiary carbon atoms such as a tert-butyl group. In addition, like 5-isopropylisophthalic acid, an alkyl group having a branched structure may be directly bonded to a benzene ring, or like 5-isopropyloxyisophthalic acid, an alkyl group having a branched structure may be bonded to a benzene ring via oxygen atoms.

Another preferable embodiment of the first porous polymer metal complex of the present invention is a porous polymer metal complex which contains an isophthalic acid ligand having a substituted amino group at position 5. This porous polymer metal complex enables selective adsorption, separation, and storage of carbon dioxide gas, and is thus appropriate. The isophthalic acid having a substituted amino group at position 5 will be described. The substituted amino group is a group in which one or two carbon-containing substituents are directly bonded to an amino group. In a case where there are two carbon-containing substituents, the substituents may be the same or may be different from each other. Otherwise, the substituents may form a ring. As the carbon-containing substituent, a substituted or unsubstituted alkyl group, a substituted or unsubstituted aryl group, an aralkyl group, and the like may be employed. The number of carbon atoms of the alkyl group is preferably 1 to 4, and is more preferably 1 to 2 in terms of a large carbon dioxide adsorption amount. As the aryl group, a phenyl group is preferable in terms of a large carbon dioxide adsorption amount. A cyclic amino group indicates that 3 to 7 carbon atoms form a cyclic structure, and is particularly preferably a ring formed of 3 to 5 carbon atoms.

As specific examples of the isophthalic acid having a substituted amino group at position 5, 5-N-methylamino isophthalic acid, 5-N,N-dimethylamino isophthalic acid, 5-N-ethylamino isophthalic acid, 5-N,N-diethylamino isophthalic acid, and 5-N,N-methylethylamino isophthalic acid may be exemplified as an isophthalic acid having a substituted or unsubstituted alkyl group, pyrrolidine-1-ylisophthalic acid may be exemplified as an isophthalic acid having a cyclic alkyl group, 5-N-phenylamino isophthalic acid, 5-(para-hydroxy)phenylamino isophthalic acid, 5-N,N-diphenylamino isophthalic acid, and 5-N,N-phenylmethylamino isophthalic acid may be exemplified as an isophthalic acid having a substituted or unsubstituted aryl group, and 5-N,N-benzylamino isophthalic acid may be exemplified as an isophthalic acid having an aralkyl group. In terms of a particularly small methane adsorption amount, 5-N,N-dimethylamino isophthalic acid and 5-N,N-diethylamino isophthalic acid are particularly preferable.

X is two or more types, and for example, may be three types or four types. Although there is no upper limit, in general, each of the positions of the six-membered ring included in the Kagome network may be probabilistically occupied by a single type of substituent, and six types are preferable to easily enhance properties.

The amount of at least one type of X is 5 mol % to 95 mol % with respect to the total number of moles of X. It is preferable that each type of X be contained at a proportion of 5 mol % or higher with respect to the total number of moles of X. The upper limit of the amount of each type of X is determined by the sum of the lower limits of the other types of X. A preferable amount of each type of X is dependent on the types and combination of X to be solutionized. For example, there may be cases where the lower limit thereof is 10 mol % or higher, is preferably 20 mol % or higher, and is more preferably 30 mol % or higher.

In addition, in the porous polymer metal complex of the present invention, interpenetration of the Kagome structure is not observed.

A representative first porous polymer metal complex of the present invention is a compound that is expressed by the following Formula (2) and has a so-called Kagome structure illustrated in FIG. 1.

(in the Formula, each of X and Y is isophthalic acid ions or isophthalic acid ions having a substituent at position 5, and X and Y are different from each other. In addition, 0.05≤m≤0.95 is satisfied. In addition, n represents the assembly number of constituent units expressed by $CuX_{1-m}Y_m$ and is not particularly limited.)

Here, X and Y are selected from the above-described X, but X and Y are different from each other. A mixing ratio m of the X and Y may be arbitrarily determined in a range of 0.05≤m≤0.95. Preferably, 0.1≤m≤0.9 is satisfied.

Since the first porous polymer metal complex of the present invention is a porous body, when the first porous polymer metal complex comes into contact with water, alcohol, or organic molecules such as ether, the first porous polymer metal complex contains water or an organic solvent in its pores and may be changed to a composite complex expressed by, for example, Formula (3):

(in the Formula, X is two or more types of isophthalic acids selected from the group consisting of isophthalic acid ions and isophthalic acid ions having a substituent at position 5, and at least one type thereof occupies 5 mol % to 95 mol % of the total number of moles of X. G represents water, alcohol, or organic molecules such as ether adsorbed into the pores, and z is an arbitrary real number.)

However, water, alcohol, or organic molecules such as ether in the composite complex are merely weakly bonded to the porous polymer metal complex and thus are removed by a pre-treatment such as drying under reduced pressure when the porous polymer metal complex is used as a gas adsorbent, and the porous polymer metal complex is restored to the complex expressed by the original Formula (1). Therefore, the complex expressed by the Formula (3) may also be regarded as intrinsically the same material as the porous polymer metal complex of the present invention.

In addition, copper ions in the first porous polymer metal complex of the present invention have a so-called paddle-wheel structure in which four oxygen atoms of carboxylic acids are coordinated to a copper ion. In many cases, copper ions may employ a 6-coordination structure, that is, the paddle-wheel structure may have two more coordinate bonds in addition to the four oxygen atoms of the carboxylic acids. For example, the porous polymer metal complex may be changed to a composite complex expressed by Formula (4):

(here, in the Formula, X is two or more types of isophthalic acid ions selected from the group consisting of isophthalic acid ions and isophthalic acid ions having a substituent at position 5, and at least one type thereof occupies 5 mol % to 95 mol % of the total number of moles of X. Q represents water molecules and the like coordinated to the copper ions that form the paddle-wheel, and p is 1 or 2.)

However, Q in the composite complex is merely weakly bonded to copper ions and thus is removed by a pre-treatment such as drying under reduced pressure when the porous polymer metal complex is used as a gas adsorbent, and the porous polymer metal complex is restored to the complex expressed by the original Formula (1). Therefore, the complex expressed by the Formula (4) may also be regarded as intrinsically the same material as the porous polymer metal complex of the present invention.

The compound expressed by the Formula (1) can be produced by dissolving copper salt and X in a solvent to be mixed in a solution state. When a protic solvent such as water or alcohol is used as the solvent for dissolving copper salt is used, preferable results can be obtained. The protic solvent such as water or alcohol allows copper salt to be appropriately dissolved therein and further forms coordinate bonds or hydrogen bonds to copper ions or counterions, thereby stabilizing copper salt. Accordingly, rapid reactions with a ligand are suppressed and side reactions are suppressed.

As examples of the alcohol, aliphatic monohydric alcohols such as methanol, ethanol, 1-propanol, 2-propanol, 1-butanol, and 2-butanol, and aliphatic dihydric alcohols such as ethylene glycol may be exemplified. In terms of low cost and high solubility of nickel salt, methanol, ethanol, 1-propanol, 2-propanol, and ethylene glycol are preferable. In addition, such alcohols may be used alone, or a plurality of types thereof may be mixed for use.

It is preferable that, as the solvent, a mixture of the above-mentioned alcohols, and an organic solvent other than the alcohols or water be used. A mixing ratio (alcohol: organic solvent other than alcohol or water) is arbitrarily set in a range of 1:100 to 100:0 (volume ratio). It is preferable that the mixing ratio of the alcohols be 30% or higher from the viewpoint of enhancement in solubility of copper salt and a ligand.

As the organic solvent, an organic solvent having high polarity is preferable in terms of excellent solubility. Specifically, dialkylformamides such as tetrahydrofuran, acetonitrile, dioxane, acetone, dimethylformamide, and diethylformamide, dialkylacetamides such as dimethylacetamide and diethylacetamide, dimethyl sulfoxide, and the like may be employed.

As the copper salt used to produce the porous polymer metal complex of the present invention, a salt containing a divalent copper ion may be used. In terms of high solubility in a solvent, copper nitrate, copper borofluoride, copper acetate, copper sulfate, copper formate, copper fumarate, copper chloride, and copper bromide are preferable. Among these, in terms of high reactivity, copper nitrate, copper borofluoride, and copper sulfate are particularly preferable.

In the porous polymer metal complex of the present invention, the porous polymer metal complex contains a mixture of two or more types of isophthalic acids or isophthalic acid derivatives having a substituent at position 5. The content ratio may be obtained by using two or more types of isophthalic acids or isophthalic acid derivatives, which are used as the raw material to synthesize the porous polymer metal complex, at a desired ratio.

During the production of the first porous polymer metal complex of the present invention, a base may be added as a reaction accelerator. As the base, for example, as an inorganic base, lithium hydroxide, sodium carbonate, potassium carbonate, sodium hydroxide, potassium hydroxide, and the like may be exemplified. As an organic base, trimethylamine, diethyl isopropyl amine, pyridine, 2,6-lutidine, and the like may be exemplified. In terms of high reaction acceleration, lithium hydroxide, sodium carbonate, sodium hydroxide, and pyridine are preferable.

With respect to the total number of moles of the isophthalic acid which is used, the addition amount thereof is preferably 0.1 moles to 6.0 moles in terms of significant reaction acceleration effect, and is more preferably 0.5 moles to 4.0 moles in terms of low side reaction.

In order to allow the copper salt solution and a ligand to react with each other, in addition to a method of loading the copper salt and the ligand in a container and thereafter adding a solvent thereto, after separately preparing the copper salt and the ligand as solutions, the solutions may be mixed with each other. The method of mixing the solutions may be performed by adding the ligand solution to the copper salt solution or may be performed in the reverse order. In addition, the mixing method may not be necessarily performed using the solutions, and for example, various methods, for example, a method of injecting a solid ligand into a copper salt solution and simultaneously pouring the resultant into a solution and a method of loading copper salt in a reactor, injecting a ligand solid or solution thereinto, and further injecting a solution for dissolving the copper salt thereinto, are possible as long as reactions finally occur substantially in solutions. However, a method of dropping a copper salt solution and a ligand solution to be mixed with each other is performed by the industrially simplest operation and is thus preferable.

Regarding the concentration of the solutions, the concentration of the metal salt solution is 40 mmol/L to 4 mol/L, and is preferably 80 mmol/L to 2 mol/L. The concentration of the organic solution of the ligand is 40 mmol/L to 3 mol/L, and is preferably 80 mmol/L to 1.8 mol/L. Reactions performed at lower concentration than the above concentration are not preferable because the production efficiency is reduced although target products can be obtained. In addition, higher concentration than the above concentration are not preferable because the adsorption capacity is degraded.

The reaction temperature is −20° C. to 180° C., and is preferably 25° C. to 140° C. Reactions performed at a lower temperature than the above temperatures are not preferable because the solubility of the raw material is reduced. Reactions may also be performed at a higher temperature by using an autoclave or the like. However, the yield is not significantly enhanced with energy cost consumed due to heating, and thus performing at the higher temperature than the above-described temperature is substantially meaningless.

A mixing ratio of the copper salt and the organic ligand used in the reactions is a molar ratio of 3:1 to 1:5, and preferably in a range of a molar ratio of 1.5:1 to 1:3. Outside of the above range, the yield of the target products is reduced, and unreacted raw materials remain. Therefore, it becomes difficult to acquire target products.

Reactions may be performed by using a typical glass-lined reactor made of SUS and a mechanical stirrer. After the reactions end, the resultant is dried to be separated into a target material and the raw material, thereby producing the target material having a high purity.

Whether or not the porous polymer metal complex obtained through the reactions has the Kagome structure can be checked by analyzing reflection obtained through single-crystal X-ray crystallography. In addition, this can also be checked by the reflection pattern of powder X-ray analysis.

Whether or not the porous polymer metal complex obtained through the reactions is porous can be checked by TG measurement. For example, this can be checked by whether or not a weight reduction is 3% to 25% in a temperature range of room temperature to 200° C. through measurement in a nitrogen atmosphere (a flow rate of 50 mL/min) at a rate of temperature increase of 5° C./min.

The gas adsorption capacity of the porous polymer metal complex obtained through the reactions may be measured by using a commercially available gas adsorption device.

Whether or not the porous polymer metal complex obtained through the reactions contains a mixture of two or more types of ligands can be checked by using infrared spectrometry, or after allowing the porous polymer metal complex to react with EDTA or the like in a solution or after decomposing and deriving the porous polymer metal complex into an ester using methanol, sulfuric acid, and the like, measuring the recovered ligand or the ester of the ligand through proton nuclear magnetic resonance (NMR).

By mixing two or more types of substituents at an appropriate ratio, the gas adsorption properties of the Kagome type porous polymer metal complex can be controlled. In this mechanism, since two types of substituents are present in the pore walls at a predetermined or higher ratio, it is thought that the different substituents interact with each other and increase the gas adsorption amount. However, in a case where one type of the substituents is a tert-butyl group which has a large volume, it is thought that pores are blocked or the like and thus a phenomenon in which carbon dioxide gas having high diffusibility is adsorbed and the other gases are not adsorbed may occur.

Although the gas adsorption properties can be controlled by mixing two or more types of substituents at an appropriate ratio, the primary advantage is the enhancement effect. This is an effect of, for example, increasing the gas storage amount or enhancing gas separation properties. As another effect, there is an effect of continuously changing gas adsorption properties. This is an effect of gradually changing the gas storage amount or separation properties by gradually changing the ratio of raw materials. Due to this effect, desired gas storage properties or separation properties can be realized in a tailor-made manner.

(2) Second Porous Polymer Metal Complex

A second porous polymer metal complex of the present invention is a compound that is expressed by the following Formula (21) and has a so-called Kagome structure illustrated in FIG. 1.

(in the Formula, X is isophthalic acid ions having a substituted amino group at position 5. n represents the assembly number of constituent units expressed by CuX and is not particularly limited.)

Figure 3:
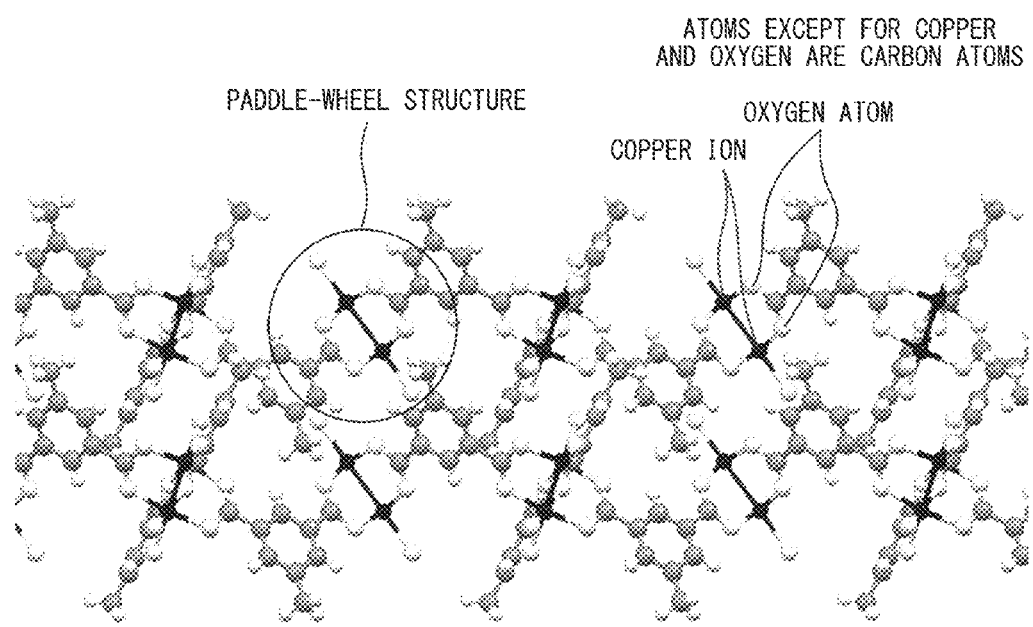
FIG. 3 is a side view of two layers of the crystal structure of the porous polymer metal complex illustrated in FIG. 1 and illustrates a stacked form of layer-like materials of the Kagome structure.

Like the first porous polymer metal complex, the second porous polymer metal complex of the present invention has the structure illustrated in FIGS. 1 to 3.

The compound of the present invention has the above-described so-called Kagome network structure as illustrated in FIG. 1, which is formed from copper ions and an isophthalic acid having a substituted amino group at position 5. The key factor here is the topology of the network, and an individual bond angle is not always the same as the bond angle in the figure because this compound has flexibility. In addition, regarding the stacked form of FIG. 3, two-dimensional Kagome networks are stacked only by weak interactions such as hydrogen bonds and van der Waals forces, and thus there is a possibility that the stacked state may be out of alignment. However, this is also regarded as the same compound having the same function.

Since the second porous polymer metal complex of the present invention is a porous body, when the second porous polymer metal complex comes into contact with water, alcohol, or organic molecules such as ether, the second porous polymer metal complex contains water or an organic solvent in its pores and may be changed to a composite complex expressed by, for example, Formula (22):

(in the Formula, X is isophthalic acid ions having a substituted amino group at position 5. n represents the assembly number of constituent units expressed by CuX and is not particularly limited. G represents water, alcohol, or organic molecules such as ether adsorbed into the pores, and m is an arbitrary number.)

However, water, alcohol, or organic molecules such as ether in the composite complex are merely weakly bonded to the porous polymer metal complex and thus are removed by a pre-treatment such as drying under reduced pressure when the porous polymer metal complex is used as a gas adsorbent, and the porous polymer metal complex is restored to the complex expressed by the original Formula (21). Therefore, the complex expressed by the Formula (22) may also be regarded as intrinsically the same material as the porous polymer metal complex of the present invention.

In addition, copper ions in the second porous polymer metal complex of the present invention have a so-called paddle-wheel structure in which four oxygen atoms of carboxylic acids are coordinated to a copper ion. In many cases, copper ions may employ a 6-coordination structure, that is, the paddle-wheel structure may have two more coordinate bonds in addition to the four oxygen atoms of the carboxylic acids. For example, the porous polymer metal complex may be changed to a composite complex expressed by Formula (23):

(in the Formula, X is isophthalic acid ions having a substituted amino group at position 5. n represents the assembly number of constituent units expressed by CuX and is not particularly limited. Q represents molecules and the like coordinated to the copper ions that form the paddle-wheel, and z is 1 or 2.)

However, Q in the composite complex is merely weakly bonded to copper ions and thus is removed by a pre-treatment such as drying under reduced pressure when the porous polymer metal complex is used as a gas adsorbent, and the porous polymer metal complex is restored to the complex expressed by the original Formula (21). Therefore, the complex expressed by the Formula (23) may also be regarded as intrinsically the same material as the second porous polymer metal complex of the present invention.

The compound expressed by the Formula (21) of the present invention can be produced by dissolving copper salt and the isophthalic acid having a substituted amino group at position 5 in a solvent and mixing in a solution state. As the solvent for dissolving copper salt, the same solvent as that used for the first porous polymer metal complex may be used.

It is also preferable that, as the solvent, a mixture of the above-mentioned alcohols, and an organic solvent other than the alcohols or water be used. A preferable mixing ratio is also the same as the ratio applied in the production of the first porous polymer metal complex.

As the organic solvent to be used, the same organic solvent as that used for the first porous polymer metal complex may be used.

Even as the copper salt used to produce the porous polymer metal complex of the present invention, the same copper salt as that used for the first porous polymer metal complex may be used.

Hereinafter, the isophthalic acid having a substituted amino group at position 5 will be described. The substituted amino group is a group in which one or two carbon-containing functional groups are directly bonded to an amino group. In a case where there are two carbon-containing functional groups, the functional groups may be the same or may be different from each other. Otherwise, the functional groups may form a ring.

As the carbon-containing functional group, a substituted or unsubstituted alkyl group, a substituted or unsubstituted aryl group, an aralkyl group, and the like may be employed. The number of carbon atoms of the alkyl group is preferably 1 to 4, and is more preferably 1 to 2 in terms of a large carbon dioxide adsorption amount. As the aryl group, a phenyl group is preferable in terms of a large carbon dioxide adsorption amount. A cyclic amino group indicates that 3 to 7 carbon atoms form a cyclic structure, and is particularly preferably a ring formed of 3 to 5 carbon atoms. As specific examples of the isophthalic acid having a substituted amino group at position 5, 5-N-methylamino isophthalic acid, 5-N,N-dimethylamino isophthalic acid, 5-N-ethylamino isophthalic acid, 5-N,N-diethylamino isophthalic acid, and 5-N,N-methylethylamino isophthalic acid may be exemplified as an isophthalic acid having a substituted or unsubstituted alkyl group, pyrrolidine-1-ylisophthalic acid may be exemplified as an isophthalic acid having a cyclic alkyl group, 5-N-phenylamino isophthalic acid, 5-(para-hydroxy) phenylamino isophthalic acid, 5-N,N-diphenylamino isophthalic acid, and 5-N,N-phenylmethylamino isophthalic acid may be exemplified as an isophthalic acid having a substituted or unsubstituted aryl group, and 5-N,N-benzylamino isophthalic acid may be exemplified as an isophthalic acid having an aralkyl group. In terms of a particularly small methane adsorption amount, 5-N,N-dimethylamino isophthalic acid and 5-N,N-diethylamino isophthalic acid are particularly preferable.

The second porous polymer metal complex which has the Kagome structure as the basic skeleton and contains the isophthalic acid ligand having a substituted amino group at position 5 can form a so-called solid solution type porous polymer metal complex. That is, by using a mixture of a plurality of types of isophthalic acids to be used as the raw material, a porous polymer metal complex containing the plurality of types of isophthalic acids which were used was synthesized. At this time, at least one type of the plurality of types of isophthalic acids which were used as the mixture needs to be an isophthalic acid having a substituted amino group at position 5, and the amount thereof is 5 mol % or more and is preferably 20 mol % or more.

This solid solution type porous polymer metal complex is a compound that is expressed by the following Formula (24) and has a so-called Kagome structure illustrated in FIGS. 1 to 3.

$$[CuX]_n \qquad (24)$$

(in the Formula, X is two or more types of isophthalic acid ions selected from the group consisting of isophthalic acid ions and isophthalic acid ions having a substituent at position 5, and an amount of isophthalic acid ions having a substituted amino group at position 5 is 5 mol % or more. n represents the assembly number of constituent units expressed by CuX and is not particularly limited.)

It is confirmed that when copper ions and two or more types of isophthalic acid ions selected from the group consisting of isophthalic acid ions having a substituent at position 5 are combined with each other, a solid solution type porous polymer metal complex having a so-called Kagome structure illustrated in FIGS. 1 to 3 is formed. The solid solution type porous polymer metal complex of the present invention is characterized by including 5 mol % or more of isophthalic acid ions having a substituted amino group at position 5 as the isophthalic acid ions and the isophthalic acid ions having a substituent at position 5. A plurality of types of isophthalic acids which are used as the mixture may be isophthalic acids having a substituted amino group at position 5. At this time, there is no interpenetration in the Kagome structure.

In the isophthalic acid ions or the isophthalic acid ions having a substituent at position 5 which are used in the second solid solution type porous polymer metal complex of the present invention, the substituent at position 5 is a group selected from a halogen atom, a substituted or unsubstituted alkyl group, a substituted or unsubstituted alkoxy group, a substituted or unsubstituted aryl group, an aralkyl group, a substituted or unsubstituted amino group, a nitro group, an amide group, a formyl group, a carbonyl group, an ester group, an azido group, a carboxyl group, a sulfo group, a hydroxyl group, and the like. As the alkyl group, an alkyl group having 1 to 12 carbon atoms, particularly, 1 to 6 carbon atoms such as a methyl group and an ethyl group is preferable. As the substituent of the substituted alkyl group, a hydroxy group, an amino group, and the like may be employed. As the alkoxy group, an alkoxy group having 1 to 12 carbon atoms, particularly, 1 to 6 carbon atoms is preferable, and a methoxy group, an ethoxy group, and a benzyloxy group are particularly preferable. As the substituent of the substituted alkoxy group, a hydroxy group, an amino group, a dimethylamino group, and the like may be employed. As the aryl group, a phenyl group and a para-hydroxyphenyl group are preferable. As the substituted aryl group, a para-hydroxyphenyl group, a para-dimethylaminophenyl group, and the like may be employed. As the aralkyl group, a benzyl group, and a phenyl group in which any one or a plurality of o-, m-, and p-positions are substituted by a methyl group and/or an ethyl group are preferable. An unsubstituted or substituted amino group is preferable, and specifically, an amino group, a methylamino group, a dimethylamino group, an ethylamino group, a diethylamino group, a phenylamino group, and a diphenylamino group are more preferable.

Particularly, a combination of isophthalic acid ions and isophthalic acid ions having an amino group, a substituted amino group, an alkyl group, or an alkoxy group at position 5 is preferable.

In the case of the solid solution type porous polymer metal complex, X is two or more types, and for example, may be three types or four types. Although there is no upper limit, in general, each of the positions of the six-membered ring included in the Kagome network may be probabilistically substituted by a single type of substituent, and six types are preferable to easily enhance properties.

In a case where the above-described substituted amino group is employed in the substitution, compared to a case where an unsubstituted amino group is employed in the substitution, a larger amount of carbon dioxide is adsorbed. Even in comparison with other gases, the carbon dioxide adsorption amount is large, in a case where the above-described substituted amino group is employed in the substitution. This is because it is easily expected that an amino group and carbon dioxide strongly interact with each other. However, it is thought that since the substituent of the amino group has a large volume, the substituted amino group and the isophthalic acid unit are twisted and accordingly carbon dioxide is more likely to be electronically and sterically adsorbed into the pores of the main material.

The second porous polymer metal complex of the present invention can be produced in the same manner as that of the first porous polymer metal complex. In addition, whether or not the obtained porous polymer metal complex has the Kagome structure can be checked in the same manner.

(3) Third Porous Polymer Metal Complex

A third porous polymer metal complex of the present invention is a compound that is expressed by the following Formula (31) and has a so-called Kagome structure illustrated in FIGS. 1 to 3.

$$[CuX]_n \qquad (31)$$

(in the Formula, X is isophthalic acid derivative ions having a branched alkyl group or a branched alkoxy group at position 5. n represents the assembly number of constituent units expressed by CuX and is not particularly limited.)

In the porous polymer metal complex of the present invention, X is ions of isophthalic acids having a branched alkyl group or a branched alkoxy group at position 5. The porous polymer metal complex has a Kagome network structure constituted by six-membered rings and three-membered rings formed from copper ions and isophthalic acid ions having a branched alkyl group or a branched alkoxy group at position 5. The key factor here is the topology of the network, and an individual bond angle is not always the same as the bond angle in the figure because this compound has flexibility. In addition, regarding the stacked form of FIG. 9A, two-dimensional Kagome networks are stacked only by weak interactions such as hydrogen bonds and van der Waals forces, and thus there is a possibility that the stacked state may be out of alignment. However, this is also regarded as the same compound having the same function.

Figure 9A:
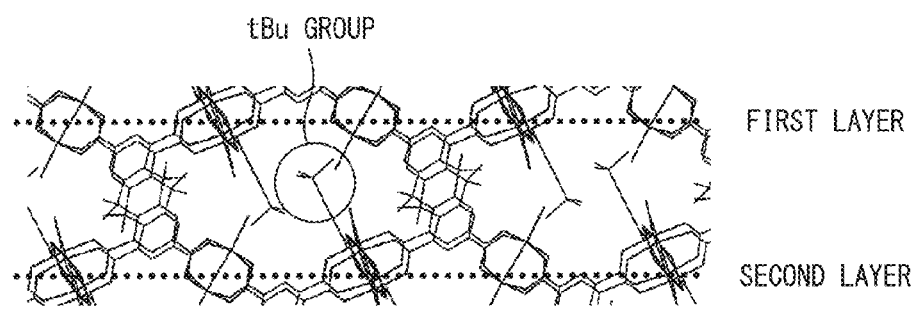
FIG. 9A is a side view of two layers of the crystal structure of the porous polymer metal complex illustrated in FIG. 1 and illustrates a stacked form of layer-like materials of the Kagome structure in a case where a substituent at position 5 is tBu.
Figure 9B:
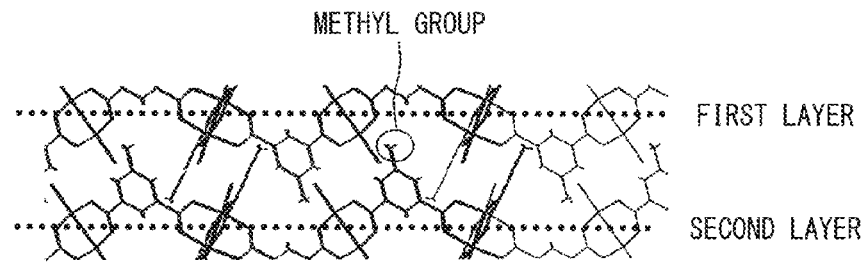
FIG. 9B is a side view of two layers of the crystal structure of the porous polymer metal complex in a case where a substituent at position 5 is methyl, and illustrates a stacked form of layer-like materials of the Kagome structure in order to compare.

Referring to FIGS. 9A and 9B, FIG. 9A illustrates a porous polymer metal complex in which the substituent at position 5 is a tBu (tert-butyl) group, and FIG. 9B illustrates a porous polymer metal complex in which the substituent at position 5 is a Me (methyl group). Compared to the Me group, the tBu groups have a large interlayer distance because the tBu groups collide with each other.

The characteristic of the third porous polymer metal complex of the present invention is that two copper ions form a so-called paddle-wheel connection and as a result, form a so-called Kagome type two-dimensional network. The third porous polymer metal complex is characterized in that the two-dimensional Kagome networks are stacked. A slight distortion of the Kagome network or the stacked state of the stacked body may be changed because the present material contains flexible organic molecules. Even in this case, they belong to the porous polymer metal complex of the present invention as long as the Kagome network structure is maintained. In addition, in the present invention, the absence of interpenetration in the Kagome structure is checked by single-crystal X-ray analysis and powder X-ray analysis.

Since the third porous polymer metal complex of the present invention is a porous body, when the third porous polymer metal complex comes into contact with water, alcohol, or organic molecules such as ether, the third porous polymer metal complex contains water or an organic solvent in its pores and may be changed to a composite complex expressed by, for example, Formula (32):

$$[CuX]_n(G)m \quad (32)$$

(in the Formula, X is isophthalic acid ions having a branched alkyl group at position 5 or isophthalic acid ions having a branched alkoxy group at position 5, and n represents the assembly number of constituent units expressed by CuX and is not particularly limited. G represents water, alcohol, or organic molecules such as ether adsorbed into the pores, and m is an arbitrary number.)

However, water, alcohol, or organic molecules such as ether in the composite complex are merely weakly bonded to the porous polymer metal complex and thus are removed by a pre-treatment such as drying under reduced pressure when the porous polymer metal complex is used as a gas adsorbent, and the porous polymer metal complex is restored to the complex expressed by the original Formula (31). Therefore, the complex expressed by the Formula (32) may also be regarded as intrinsically the same material as the porous polymer metal complex of the present invention.

In addition, copper ions in the porous polymer metal complex of the present invention have a so-called paddle-wheel structure in which four oxygen atoms of carboxylic acids are coordinated to a copper ion. In many cases, copper ions may employ a 6-coordination structure, that is, the paddle-wheel structure may have two more coordinate bonds in addition to the four oxygen atoms of the carboxylic acids. For example, the porous polymer metal complex may be changed to a composite complex expressed by Formula (33):

$$[CuXQ_z]_n \quad (33)$$

(in the Formula, X is isophthalic acid ions having a branched alkyl group at position 5 or isophthalic acid ions having a branched alkoxy group at position 5. n represents the assembly number of constituent units expressed by CuX and is not particularly limited. Q represents molecules and the like coordinated to the copper ions that form the paddle-wheel, and z is 1 or 2.) However, Q in the composite complex is merely weakly bonded to copper ions and thus is removed by a pre-treatment such as drying under reduced pressure when the porous polymer metal complex is used as a gas adsorbent, and the porous polymer metal complex is restored to the complex expressed by the original Formula (31). Therefore, the complex expressed by the Formula (33) may also be regarded as intrinsically the same material as the third porous polymer metal complex of the present invention.

The third porous polymer metal complex expressed by the Formula (31) of the present invention can be produced in the same manner as that of the first porous polymer metal complex by dissolving copper salt and the isophthalic acid having a branched alkyl group at position 5 or the isophthalic acid having a branched alkoxy group at position 5 in a solvent to be mixed in a solution state.

As the isophthalic acid having a branched alkyl group at position 5, which is used in the present invention, 5-isopropylisophthalic acid, 5-isobutylisophthalic acid, 5-tert-butylisophthalic acid, 5-(2-pentyl)isophthalic acid, 5-(3-pentyl)isophthalic acid, 5-(2-hexyl)isophthalic acid, 5-(3-hexyl)isophthalic acid, and the like may be exemplified.

In addition, as the isophthalic acid having a branched alkoxy group at position 5, 5-isopropyloxyisophthalic acid, 5-isobutyloxyisophthalic acid, 5-tert-butyloxyisophthalic acid, 5-(2-pentyl)oxyisophthalic acid, 5-(3-pentyl)oxyisophthalic acid, 5-(2-hexyl)oxyisophthalic acid, 5-(3-hexyl)oxyisophthalic acid, and the like may be exemplified.

A branched alkyl group or branched alkoxy group having 3 or 4 carbon atoms is preferably used, and in terms of a large gas adsorption amount, 5-isopropylisophthalic acid, 5-isobutylisophthalic acid, 5-tert-butylisophthalic acid, 5-isopropyloxyisophthalic acid, 5-isobutyloxyisophthalic acid, and 5-tert-butyloxyisophthalic acid are preferable.

As in the above exemplification, it is important for the alkyl portion of the alkyl group or the alkoxy group to have a branched structure, and the branched structure may be a branched structure having secondary carbon atoms such as an isobutyl group or a branched structure having tertiary carbon atoms such as a tert-butyl group. In addition, like 5-isopropylisophthalic acid, an alkyl group having a branched structure may be directly bonded to a benzene ring, or like 5-isopropyloxyisophthalic acid, an alkyl group having a branched structure may be bonded to a benzene ring via oxygen atoms.

It was confirmed that the third porous polymer metal complex of the present invention can form a so-called solid solution type porous polymer metal complex. That is, by using a mixture of a plurality of types of isophthalic acids as the raw material, a porous polymer metal complex containing the plurality of types of isophthalic acids which were used was synthesized. At this time, at least one type of the plurality of types of isophthalic acids which are used as the mixture needs to have a branched structure, and the amount thereof is 5 mol % or more and is preferably 20 mol % or more.

This solid solution type porous polymer metal complex is a compound that is expressed by the following Formula (34) and has a so-called Kagome structure illustrated in FIGS. 1 to 3.

$$[CuX]_n \quad (34)$$

(in the Formula, X represents two or more types of isophthalic acid ions selected from the group consisting of isophthalic acid ions and isophthalic acid ions having a substituent at position 5 and isophthalic acid derivative ions having a branched alkyl group or a branched alkoxy group at position 5 substitute 5 mol % or more. n represents the assembly number of constituent units expressed by CuX and is not particularly limited.)

It is confirmed that when copper ions and two or more types of isophthalic acid ions selected from the group consisting of isophthalic acid ions and isophthalic acid ions having a substituent at position 5 are combined with each other, a solid solution type porous polymer metal complex having a so-called Kagome structure illustrated in FIGS. 1 to 3 is formed. The third solid solution type porous polymer metal complex of the present invention is characterized by 5 mol % or more of isophthalic acid derivative ions having a branched alkyl group or a branched alkoxy group at position 5 as isophthalic acid ions or isophthalic acid ions having a substituent at position 5.

In the isophthalic acid ions having a substituent at position 5 which are used in the third solid solution type porous polymer metal complex of the present invention, the substituent at position 5 is a group selected from a halogen atom, a substituted or unsubstituted alkyl group, a substituted or unsubstituted alkoxy group, a substituted or unsubstituted aryl group, an aralkyl group, a substituted or unsubstituted amino group, a nitro group, an amide group, a formyl group, a carbonyl group, an ester group, an azido group, a carboxyl group, a sulfo group, a hydroxyl group, and the like.

As the alkyl group, an alkyl group having 1 to 12 carbon atoms, particularly, 1 to 6 carbon atoms such as a methyl group and an ethyl group is preferable. As the substituent of the substituted alkyl group, a hydroxy group, an amino group, and the like may be employed.

As the alkoxy group, an alkoxy group having 1 to 12 carbon atoms, particularly, 1 to 6 carbon atoms is preferable, and a methoxy group, an ethoxy group, and a benzyloxy group are particularly preferable. As the substituent of the substituted alkoxy group, a hydroxy group, an amino group, a dimethylamino group, and the like may be employed.

As the aryl group, a phenyl group and a para-hydroxyphenyl group are preferable. As the substituted aryl group, a para-hydroxyphenyl group, a para-dimethylaminophenyl group, and the like may be employed.

As the aralkyl group, a benzyl group, and a phenyl group in which any one or a plurality of o-, m-, and p-positions are substituted by a methyl group and/or an ethyl group are preferable.

As the unsubstituted or substituted amino group, an amino group, a mono- or dialkylamino group (the number of carbon atoms of an alkyl group is preferably 1 to 4, and is more preferably 1 to 2 in terms of a small methane adsorption amount) such as methylamino group, dimethylamino group, ethylamino group, and diethylamino group, and a mono- or diaryl group such as a phenylamino group and a diphenylamino group are preferable.

In the third porous polymer metal complex of the present invention, a combination of isophthalic acid ions having a branched alkyl group or a branched alkoxy group at position 5, and isophthalic acid ions, isophthalic acid ions having an unbranched alkyl group or a unbranched alkoxy group at position 5, isophthalic acid ions having an alkoxy group at position 5, or isophthalic acid derivative ions having an unsubstituted or substituted amino group at position 5 is preferable.

In the case of the solid solution type porous polymer metal complex, X is two or more types, and for example, may be three types or four types. Although there is no upper limit, in general, each of the positions of the six-membered ring included in the Kagome network may be probabilistically substituted by a single type of substituent, and six types are preferable to easily enhance properties.

During the production of the third porous polymer metal complex of the present invention, a base may be added as a reaction accelerator. As the base, the same base as that used to produce the first porous polymer metal complex may be used.

Reactions between a copper salt solution and ligands may be performed in the same manner as that of the first porous polymer metal complex.

Whether or not the porous polymer metal complex obtained through the reactions has the Kagome structure can be determined by single-crystal X-ray crystallography.

In addition, whether or not the third porous polymer metal complex obtained through the reactions has the Kagome structure can also be checked in the same manner as that of the first porous polymer metal complex. Whether or not the third porous polymer metal complex obtained through the reactions is porous can be checked in the same manner as that of the first porous polymer metal complex.

(4) Fourth Porous Polymer Metal Complex

A fourth porous polymer metal complex of the present invention is a compound that is expressed by the following Formula (41) and has a so-called Kagome structure illustrated in FIGS. 1 to 3.

$[CuX]_n$             (41)

(in the Formula, X represents isophthalic acid derivative ions in which position 5 is substituted by a perfluoroalkyl group containing 3 to 21 fluorine atoms or by a perfluoroalkoxy group containing 3 to 21 fluorine atoms. n represents the assembly number of constituent units expressed by CuX and is not particularly limited.)

The compound of the present invention has the above-described so-called Kagome network structure as illustrated in FIG. 1, which is formed from copper ions and an isophthalic acid derivative in which a perfluoroalkyl group containing 3 to 21 fluorine atoms or a perfluoroalkoxy group containing 3 to 21 fluorine atoms substitutes position 5. The key factor here is the topology of the network, and an individual bond angle is not always the same as the bond angle in the figure because this compound has flexibility. In addition, regarding the stacked form of FIG. 3, two-dimensional Kagome networks are stacked only by weak interactions such as hydrogen bonds and van der Waals forces, and thus there is a possibility that the stacked state may be out of alignment. However, this is also regarded as the same compound having the same function.

Since the porous polymer metal complex of the present invention is a porous body, when the porous polymer metal complex comes into contact with water, alcohol, or organic molecules such as ether, the porous polymer metal complex contains water or an organic solvent in its pores and may be changed to a composite complex expressed by, for example, Formula (42):

$[CuX]_n(G)_m$          (42)

(in the Formula, X represents isophthalic acid ions in which position 5 is substituted by a group selected from the group consisting of a perfluoroalkyl group containing 3 to 21 fluorine atoms or by a perfluoroalkoxy group containing 3 to 21 fluorine atoms. n represents the assembly number of constituent units expressed by CuX and is not particularly limited.)

However, water, alcohol, or organic molecules such as ether in the composite complex are merely weakly bonded to the porous polymer metal complex and thus are removed by a pre-treatment such as drying under reduced pressure when the porous polymer metal complex is used as a gas adsorbent, and the porous polymer metal complex is restored to the complex expressed by the original Formula (41). Therefore, the complex expressed by the Formula (42) may also be regarded as intrinsically the same material as the fourth porous polymer metal complex of the present invention.

In addition, copper ions in the fourth porous polymer metal complex of the present invention have a so-called paddle-wheel structure in which four oxygen atoms of carboxylic acids are coordinated to a copper ion. In many cases, copper ions may employ a 6-coordination structure, that is, the paddle-wheel structure may have two more coordinate bonds in addition to the four oxygen atoms of the carboxylic acids. For example, the porous polymer metal complex may be changed to a composite complex expressed by Formula (43):

$$[CuXQ_z]_n \qquad (43)$$

(in the Formula, X represents isophthalic acid derivative ions in which position 5 is substituted by a perfluoroalkyl group containing 3 to 21 fluorine atoms or by a perfluoroalkoxy group containing 3 to 21 fluorine atoms. n represents the assembly number of constituent units expressed by CuX and is not particularly limited. Q represents molecules and the like coordinated to the copper ions that form the paddle-wheel, and z is 1 or 2.)

However, Q in the composite complex is merely weakly bonded to copper ions and thus is removed by a pre-treatment such as drying under reduced pressure when the porous polymer metal complex is used as a gas adsorbent, and the porous polymer metal complex is restored to the complex expressed by the original Formula (41). Therefore, the complex expressed by the Formula (43) may also be regarded as intrinsically the same material as the second porous polymer metal complex of the present invention.

In a method of the present invention, the compound expressed by the Formula (41) can be produced by dissolving copper salt and the isophthalic acid in which a perfluoroalkyl group containing 3 to 21 fluorine atoms or a perfluoroalkoxy group containing 3 to 21 fluorine atoms substitutes position 5, in a solvent and mixing in a solution state. As the solvent for dissolving copper salt, the same solvent as that used for the first porous polymer metal complex may be used.

It is also preferable that, as the solvent, a mixture of the above-mentioned alcohols, and an organic solvent other than the alcohols or water be used. A mixing ratio is arbitrarily set in a range of 1:100 to 100:0 (volume ratio). It is preferable that the mixing ratio of the alcohols be 30% or higher from the viewpoint of enhancement in solubility of copper salt and a ligand.

As the organic solvent to be used, the same organic solvent as that used for the first porous polymer metal complex may be used.

Even as the copper salt used in the method of the present invention, the same copper salt as that used for the first porous polymer metal complex may be used.

Hereinafter, the isophthalic acid derivative in which a perfluoroalkyl group containing 3 to 21 fluorine atoms or a perfluoroalkoxy group containing 3 to 21 fluorine atoms substitutes position 5 will be described.

The perfluoroalkyl group or perfluoroalkoxy group containing 3 to 21 fluorine atoms is a functional group (perfluoro group) in which all atoms except carbon atoms bonded to the carbon skeleton are fluorine atoms. Among a perfluoroalkyl group and a perfluoroalkoxy group having 1 to 10 carbon atoms, the perfluoroalkyl group containing 1 to 10 carbon atoms is particularly preferable. That is, the perfluoroalkyl group is a perfluoroalkyl group expressed by:

$$C_aF_{(2a+1)}$$

(in the Formula, a is an integer of 1 to 10) The alkyl group may be a linear or branched chain. The number of carbon atoms is preferably 1 to 8 in terms of high oxygen adsorption properties.

The fourth porous polymer metal complex of the present invention can form a so-called solid solution type porous polymer metal complex. That is, by mixing a plurality of types of isophthalic acids to be used as the raw material and using the mixture, a porous polymer metal complex containing a plurality of types of isophthalic acids can be synthesized. At this time, at least one type of the plurality of types of isophthalic acids which are used as a mixture is an isophthalic acid in which an alkyl group containing 3 to 21 fluorine atoms substitutes position 5 or an isophthalic acid in which an alkoxy group containing 3 to 21 fluorine atoms substitutes position 5. Particularly, the isophthalic acid in which an alkyl group containing 3 to 21 fluorine atoms substitutes position 5 is preferable.

This solid solution type porous polymer metal complex is a porous polymer metal complex characterized by being expressed by the following Formula (44):

$$[CuX]_n \qquad (44)$$

(in the Formula, X includes at least one type of non-fluorinated isophthalic acid ions selected from the group consisting of isophthalic acid ions in which position 5 is substituted by an alkyl group having 1 to 10 carbon atoms, isophthalic acid ions in which position 5 is substituted by an alkoxy group having 1 to 10 carbon atoms, and isophthalic acid ions, and at least one type of fluorinated phthalic acid derivative ions selected from the group consisting of isophthalic acid ions in which position 5 is substituted by a perfluoroalkyl group containing 3 to 21 fluorine atoms and isophthalic acid ions in which position 5 is substituted by a perfluoroalkoxy group containing 3 to 21 fluorine atoms, and the fluorinated isophthalic acid ions substitute 5 mol % or more. n represents the assembly number of constituent units expressed by CuX and is not particularly limited.)

Even in another fourth porous polymer metal complex of the present invention, the isophthalic acid ions in which position 5 is substituted by a perfluoroalkyl group containing 3 to 21 fluorine atoms and the isophthalic acid ions in which position 5 is substituted by a perfluoroalkoxy group containing 3 to 21 fluorine atoms, which are described above, may be used.

In the case of the solid solution type porous polymer metal complex, X is two or more types, and for example, may be three types or four types. Although there is no upper limit, in general, each of the positions of the six-membered ring included in the Kagome network may be probabilistically substituted by a single type of substituent, and six types are preferable to easily enhance properties.

When the fourth porous polymer metal complex of the present invention is obtained, as a reaction accelerator, an amount of the same base as that used for the first porous polymer metal complex may be used, the amount being the same as the addition amount thereof.

Reactions between a copper salt solution and ligands may be performed in the same manner as that of the first porous polymer metal complex. In addition, whether or not the obtained porous polymer metal complex has the Kagome structure can be checked in the same manner as that used to check the first porous polymer metal complex.

[Composition of Adsorbents]

The gas adsorbent of the present invention (hereinafter, referred to as an adsorbent (A)) may be used alone as an adsorbent, and may be used as a composition with another adsorbent. In a case of using adsorbents as a composition, when an adsorbent (B) which shows a behavior in which adsorption isotherm and desorption isotherm coincide with each other is used as another adsorbent, and thus the gas adsorbent can have significantly excellent adsorption properties.

Here, the adsorbent (B) is a material in which a gas pressure-gas adsorption amount curve during adsorption and a gas pressure-gas adsorption amount curve during desorption substantially coincide with each other. The adsorbent (B) is not particularly limited as long as such properties are provided, and a physical adsorbent, a chemical adsorbent, and a physicochemical adsorbent which is a combination thereof may be used.

The physical adsorbent is an adsorbent which traps molecules to be adsorbed by using a weak force such as interactions between molecules. As the physical adsorbent, activated carbon, silica gel, activated alumina, zeolite, clay, superadsorptive fiber, and a metal complex may be employed. The chemical adsorbent is an adsorbent which traps molecules to be adsorbed by strong chemical bonds. As the chemical adsorbent, calcium carbonate, calcium sulfate, potassium permanganate, sodium carbonate, potassium carbonate, sodium phosphate, and an activated metal may be employed. The physicochemical adsorbent is an adsorbent which has adsorption mechanisms of both the physical adsorbent and the chemical adsorbent. A composition of two or more types of the adsorbents may be used. However, the technical scope of the present invention is not limited to the specific examples. The shape of the adsorbent (B) is not particularly limited, and a powdered adsorbent having an average particle size of 500 μm to 5000 μm is generally used.

As the adsorbent (B), in consideration of production cost or gas adsorption performance, activated carbon is preferable. The activated carbon is relatively cheap, and has a large gas adsorption amount per mass. However, the activated carbon has poor cycle properties regarding absorption and desorption of gas, and when absorption and desorption are repeated, there is a tendency for the gas adsorption amount to be significantly reduced. Therefore, in the related art, in spite of a large gas adsorption amount per mass, it was difficult to use the activated carbon for the gas storage device or the gas separation device. Accordingly, in a case of using the activated carbon as the adsorbent (B) of the present invention, excellent gas adsorption performance of the activated carbon can be sufficiently exhibited. In addition, the activated carbon has a tendency to increase the adsorption amount with specific surface area, and thus the specific surface area of the activated carbon is preferably 1000 $m^2/g$ or higher.

In addition, it is preferable that the structure of the adsorbent (B) for use be appropriately controlled depending on gas to be adsorbed. For example, pores included in the activated carbon may be classified into super-micropores (0.8 nm or smaller), micropores (0.8 nm to 2 nm), mesopores (2 nm to 50 nm), and macropores (50 nm or greater) by the size of the pores. A gas type which is easily adsorbed varies depending on the side of the pores, and methane gas is likely to be adsorbed by micropores. Therefore, in a case where methane gas is to be adsorbed, the pore distribution of the activated carbon may be controlled so that the ratio of the micropores is high.

In a case of composing the adsorbent (A) with the adsorbent (B), the adsorbent (B) is coated with the adsorbent (A), and it is preferable that the adsorbent (B) be completely coated so as not to come into contact with outside air and be coated without cracks or incomplete coatings. However, even when several cracks and the like are present, as long as free gas adsorption of the adsorbent (B) is impeded and the adsorbent (B) which is coated with the adsorbent (A) shows similar properties to the basic properties of the adsorbent (A) regarding gas adsorption, this is included in the technical scope of the present invention. It is preferable that the adsorbent (B) be coated with 5 volume % to 50 volume % of the adsorbent (A) with respect to 100 volume % of the adsorbent (B). In addition, although the thickness of the adsorbent (A) used to coat the adsorbent (B) needs to be determined depending on the type of the adsorbent (A), when the adsorbent (A) is too thin, there is a concern that the gas adsorption properties of the adsorbent (B) may not be sufficiently controlled. On the other hand, when the adsorbent (A) is too thick, gas adsorption onto the adsorbent (B) is less likely to occur, and thus there is a concern that the total gas adsorption amount may be reduced. In consideration of this, the average thickness of the adsorbent (A) is preferably 10 μm to 100 μm. The thickness of the adsorbent (A) can be controlled by controlling the usage amount of the adsorbent (A). In addition, the thickness of the adsorbent (A) can be calculated from a cross-sectional photograph taken by using an electron microscope.

As a method of composing the adsorbents (A) and (B) with each other, (1) a method of adding, to a solvent in which the adsorbent (A) is dissolved, the adsorbent (B) which is not dissolved in the solvent, and allowing crystal growth of the adsorbent (A) so as to cause the adsorbent (A) to be attached to the adsorbent (B), (2) a method of preparing a slurry containing the adsorbent (A) and coating the surface of the adsorbent (B) with the slurry and drying the resultant so as to cause the adsorbent (A) to be attached to the adsorbent (B), and the like may be used.

EXAMPLES

The method of preparing the porous polymer metal complex varies depending on the type of gas adsorbent, and thus cannot be uniquely determined. Here, a case of synthesizing a solid solution type porous polymer metal complex by using copper, isophthalic acid, and 5-methylisophthalic acid will be exemplified.

Example 1

Figure 4:
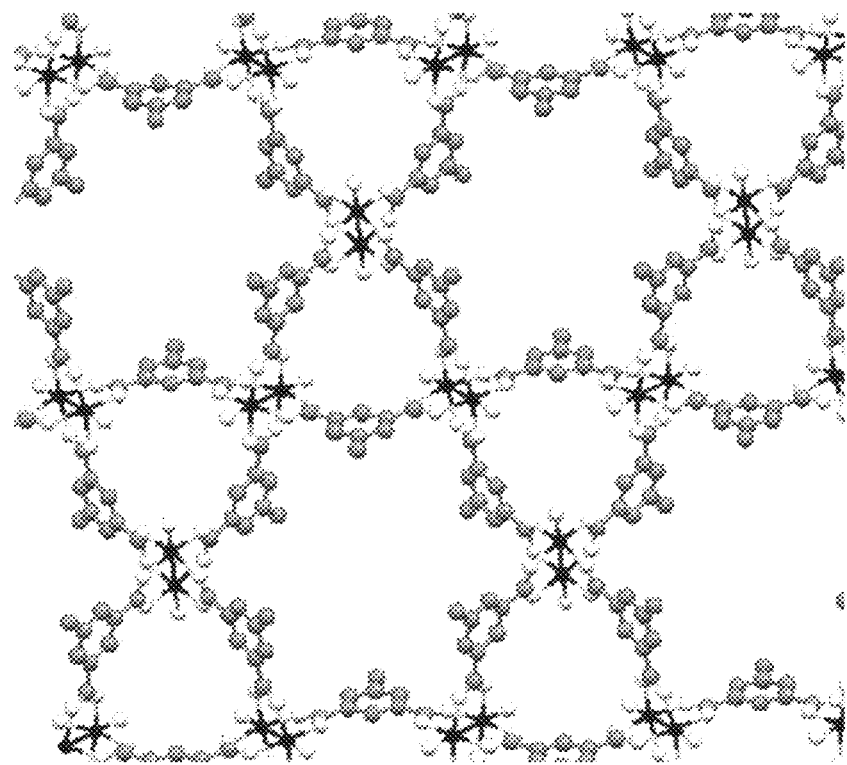
FIG. 4 illustrates the crystal structure (Kagome structure) of a porous polymer metal complex obtained in Example 1.

Isophthalic acid (0.095 mmol), 5-methylisophthalic acid (0.005 mmol), and copper nitrate trihydrate (0.10 mmol) were dispersed in 5 ml of methanol, pyridine (0.1 mmol) was added thereto, and the resultant was left at room temperature for 3 weeks, thereby obtaining a hexagonal-plate-shaped light blue single crystal. The single crystal having a diameter of about 150 μm was coated with Paratone so as not to be exposed to the air. Thereafter, a crystal diffraction image was obtained by a single-crystal measurement device manufactured by Rigaku Corporation (single-crystal structural analysis device for very small crystals, VariMax, MoKα radiation ($\lambda$=0.71069 Å), an irradiation time of 4 seconds, d=45 mm, 2θ=−20, a temperature of −180° C.), the obtained diffraction image was analyzed by using an analysis software "Yadokari XG2009", and it was confirmed that the single crystal had a Kagome structure illustrated in FIG. 4 (α=32.902, b=18.489, c=23.186; α=90.341, β=175, γ=90; space group=C2/C).

In addition, it was confirmed from analysis by single-crystal X-ray diffraction and a powder X-ray diffraction method that the Kagome structure was not in an interpenetration state.

Figure 5:
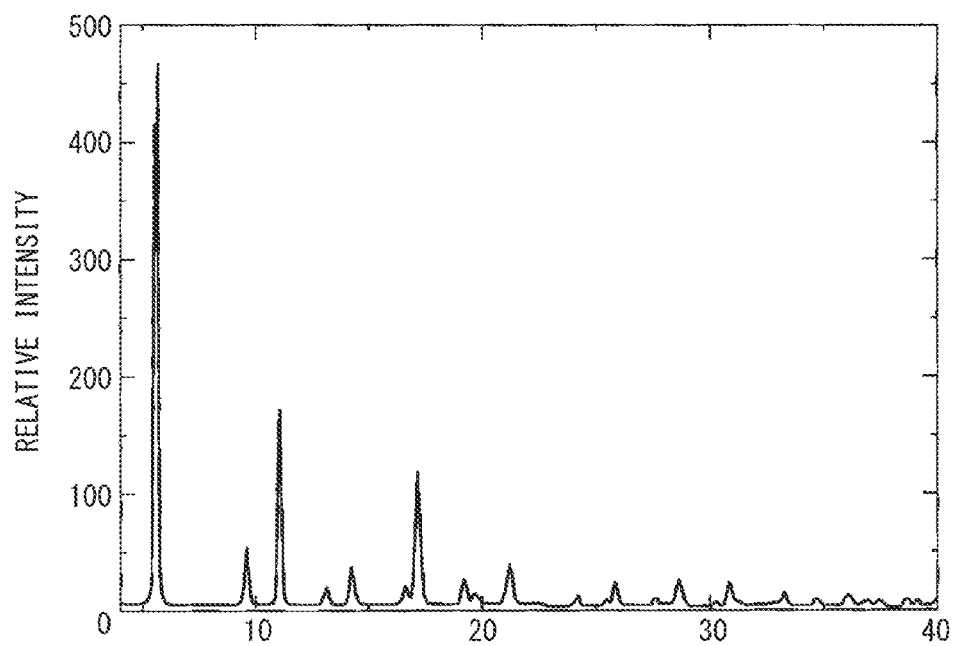
FIG. 5 illustrates a result of powder X-ray diffraction obtained by measuring powder obtained in Example 1 using a powder X-ray device.

In addition, isophthalic acid (0.95 mmol), 5-methyl-isophthalic acid (0.05 mmol), and copper nitrate trihydrate (1.00 mmol) were dispersed in 20 ml of methanol, pyridine (1 mmol) was added thereto, the container was sealed, and then the resultant was stirred at 120° C. for 1 hour. After reactions, blue powder was filtered and then was washed with methanol, thereby obtaining 174 mg of powder. A result of measuring the powder by using a powder X-ray device manufactured by Bruker AXS K.K. (DISCOVER D8 with GADDS, CuKα ($\lambda$=1.54 Å), 2θ=4 to 40 degrees, measured at room temperature) is shown in FIG. 5. As illustrated in FIG. 5, reflections occurred at 5.6 degrees, 9.6 degrees, 11.0 degrees, 12.8 degrees, 14.0 degrees, 16.5 degrees, and 17.0 degrees. The reflections were the same as those in the powder simulation pattern of the single crystal.

That is, it was confirmed that the porous polymer metal complex having a Kagome structure could be synthesized by the above-described two methods and the porous polymer metal complex could be analyzed by the single-crystal X-ray diffraction and the powder X-ray diffraction methods.

In addition, it was confirmed from the analysis by the single-crystal X-ray diffraction and the powder X-ray diffraction methods that the Kagome structure was not in an interpenetration state.

<Analysis Result of Mixing Ratio of Ligands)

50 mg of a blue solid was dispersed in methanol, several drops of concentrated sulfuric acid were added thereto, and the resultant was heated for 6 hours. The methanol was removed from the reaction mixture by a rotary evaporator, water was added to the residue, and the resultant was extracted using dichloromethane. After the dichloromethane solution was simply purified by a silica gel column, the solvent was removed, and the residue was analyzed by NMR. The ratio of the isophthalic acid to the 5-methyl-isophthalic acid was 95:5, and thus it could be confirmed that the isophthalic acid and the 5-methylisophthalic acid were contained in the solid obtained by the reactions at a ratio of 95:5.

<Confirming that Two Types of Substituents Are Dispersed Without Forming Domains to From Material in Solid Solution Form>

When two types of substituents or hydrogen, for example, ligands respectively having a substituent A and a substituent B are used as the raw material, at least two cases, that is, a case where A and B are uniformly dispersed in a porous polymer metal complex (in a solid solution state) and a case where A and B are nonuniformly dispersed and form domains, are considered.

Figure 6:
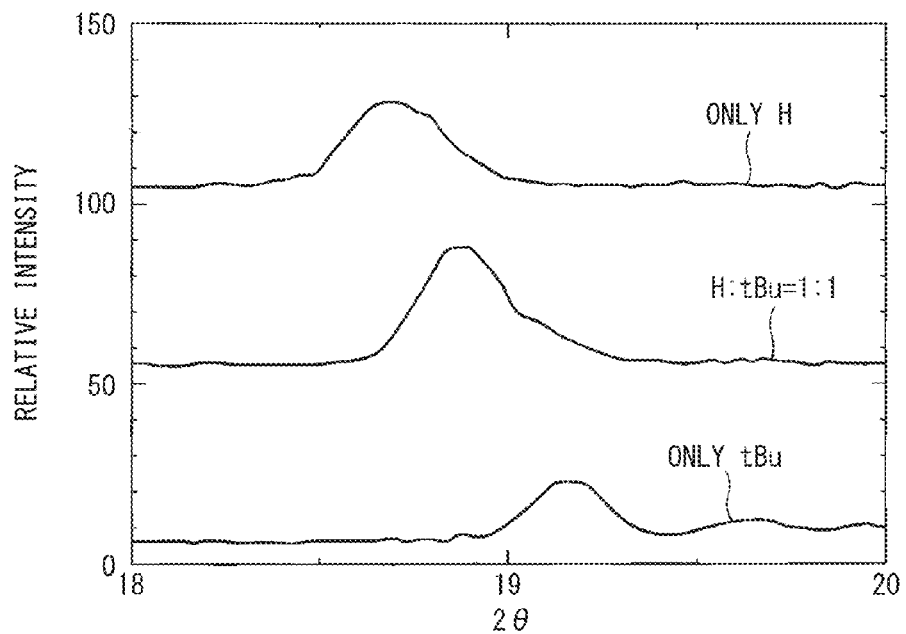
FIG. 6 illustrates a powder X-ray result of a porous polymer complex obtained by mixing a single ligand (isophthalic acid) having H at position 5 and a single ligand (5-tert-butylisophthalic acid) having a tert-butyl group at position 5 at a ratio of 1:1 for use.
Figure 7:
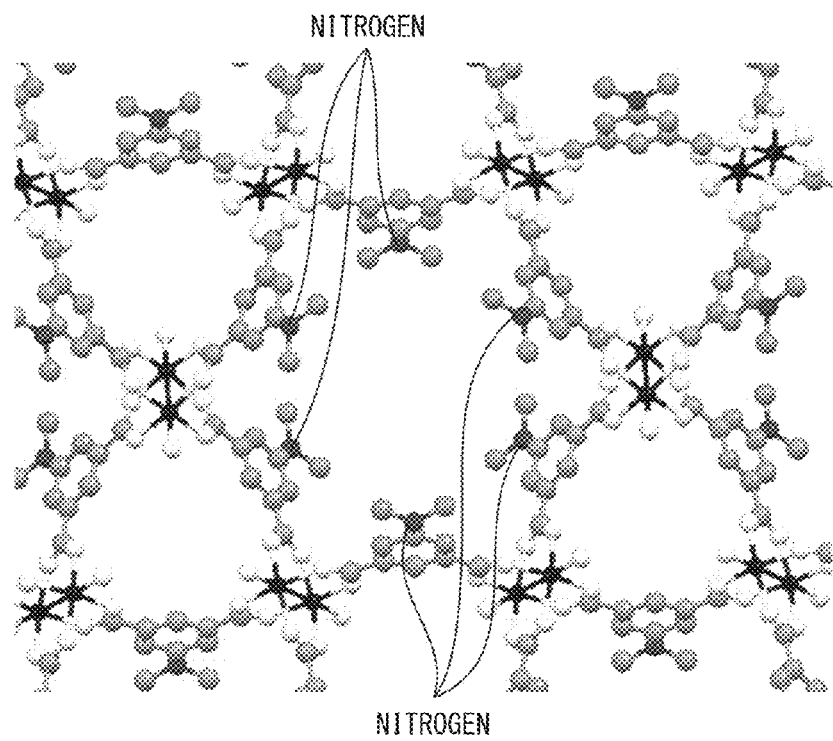
FIG. 7 illustrates the Kagome structure of a porous polymer metal complex obtained by analyzing a single crystal obtained in Example 77.
Figure 8:
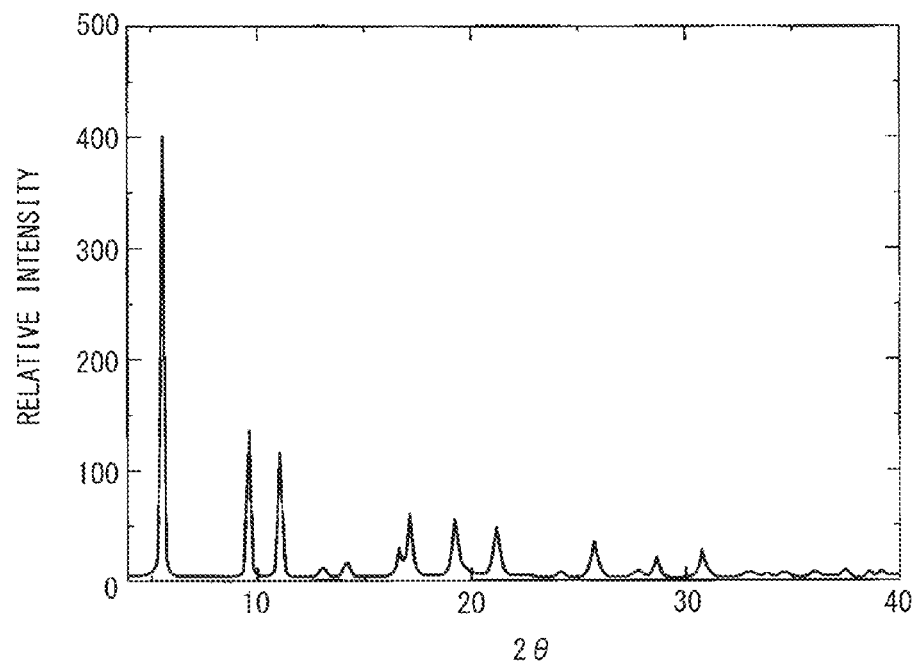
FIG. 8 illustrates a result obtained by measuring a powder obtained in Example 77 using a powder X-ray device.

The result of powder X-ray analysis of porous polymer metal complexes obtained by using only a ligand (isophthalic acid) having H at position 5, using only a ligand (5-tert-butylisophthalic acid) having a tert-butyl group at position 5, and using a mixture thereof at a ratio of 1:1 is shown in FIG. 6.

In a case of using only the isophthalic acid as the raw material, a reflection was seen at 2θ=18.7 degrees, in a case of using only the 5-tert-butylisophthalic acid as the raw material, a reflection was seen at 2θ=19.2 degrees, and in a case of using the mixture of the ligands at a ratio of 1:1 as the raw material, a reflection was seen at 2θ=18.9 degrees. Therefore, any of the reflections at 2θ=18.7 degrees and 19.2 degrees derived from the raw material, which are observed in a case where the raw material ligand forms domains, was not seen. From this, it can be seen that in a case of using the mixture of the two types of ligands, the ligands of the raw material were uniformly dispersed without forming domains, that is, were present in the porous polymer metal complex in a solid solution state.

<Result of Gas Adsorption>

The nitrogen adsorption properties of the obtained gas adsorbent at 77 K were examined. For the measurement, a BET automatic adsorption device (BELSORP-mini II manufactured by BEL Japan, Inc.) was used. Before the measurement, by drying a sample under vacuum at 393 K for 12 hours, even a small amount of solvent particles and the like that might remain were removed. The adsorption of each of gases including carbon dioxide (195 K), oxygen (77 K), and nitrogen (77 K) was measured (measurement temperature is in parentheses, and adsorption amount is measured in mL/g).

The result of Example 1 is shown in Table 1.

Examples 2 to 76 and Comparative Examples 1 to 56

Porous polymer metal complexes were synthesized in the same manner as that of Example 1 except that instead of isophthalic acid (0.095 mmol), 5-methylisophthalic acid (0.005 mmol), and copper nitrate trihydrate (0.10 mmol), ligands containing substituents A and B shown in Tables 1 to 5 were used by amounts shown in tables. The obtained powder was analyzed and evaluated by the same measurement method as that of Example 1.

The results of Examples 2 to 76 are shown in Tables 1, 2, and 3. The results of Comparative Examples 1 to 56 are shown in Tables 4 and 5.

TABLE 1

| Example | Functional group A | Functional group B | A content (%) | B content (%) | Carbon dioxide adsorption amount | Oxygen adsorption amount | Nitrogen adsorption amount |
|---|---|---|---|---|---|---|---|
| 1 | H | Me | 95 | 5 | 239 | 225 | 173 |
| 2 | H | Me | 70 | 30 | 258 | 268 | 149 |
| 3 | H | Me | 30 | 70 | 282 | 212 | 182 |
| 4 | H | Me | 10 | 90 | 276 | 198 | 179 |
| 5 | H | Me | 5 | 95 | 274 | 195 | 170 |
| 6 | H | n-Bu | 95 | 5 | 242 | 225 | 173 |
| 7 | H | n-Bu | 70 | 30 | 215 | 268 | 149 |
| 8 | H | n-Bu | 30 | 70 | 255 | 212 | 182 |
| 9 | H | n-Bu | 10 | 90 | 257 | 198 | 179 |
| 10 | H | OMe | 95 | 5 | 222 | 215 | 202 |
| 11 | H | OMe | 70 | 30 | 217 | 209 | 203 |
| 12 | H | OMe | 30 | 70 | 194 | 200 | 189 |

TABLE 1-continued

| Example | Functional group A | Functional group B | A content (%) | B content (%) | Carbon dioxide adsorption amount | Oxygen adsorption amount | Nitrogen adsorption amount |
|---|---|---|---|---|---|---|---|
| 13 | H | OMe | 10 | 90 | 189 | 254 | 174 |
| 14 | H | NMe2 | 95 | 5 | 288 | 211 | 169 |
| 15 | H | NMe2 | 70 | 30 | 279 | 198 | 192 |
| 16 | H | NMe2 | 30 | 70 | 283 | 187 | 192 |
| 17 | H | NMe2 | 10 | 90 | 299 | 200 | 179 |
| 18 | H | OH | 95 | 5 | 261 | 197 | 168 |
| 19 | H | OH | 70 | 30 | 253 | 187 | 156 |
| 20 | H | OH | 30 | 70 | 249 | 201 | 172 |
| 21 | H | OH | 10 | 90 | 263 | 179 | 161 |
| 22 | H | CO2H | 10 | 90 | 272 | 222 | 201 |
| 23 | H | CO2H | 95 | 5 | 259 | 237 | 181 |
| 24 | H | CO2H | 70 | 30 | 271 | 251 | 168 |
| 25 | H | CO2H | 30 | 70 | 288 | 219 | 181 |
| 26 | H | SO3H | 95 | 5 | 262 | 221 | 184 |
| 27 | H | SO3H | 70 | 30 | 259 | 201 | 179 |
| 28 | H | SO3H | 30 | 70 | 254 | 198 | 163 |
| 29 | H | SO3H | 10 | 90 | 232 | 199 | 171 |
| 30 | H | OMe | 95 | 5 | 172 | 221 | 163 |
| 31 | H | OMe | 70 | 30 | 198 | 231 | 159 |
| 32 | H | OMe | 30 | 70 | 252 | 194 | 152 |
| 33 | H | OMe | 10 | 90 | 201 | 187 | 177 |
| 34 | H | OMe | 5 | 95 | 198 | 188 | 170 |
| 35 | Me | OMe | 95 | 5 | 217 | 169 | 176 |
| 36 | Me | OMe | 70 | 30 | 241 | 186 | 154 |
| 37 | Me | OMe | 30 | 70 | 211 | 157 | 143 |
| 38 | Me | OMe | 10 | 90 | 196 | 152 | 144 |
| 39 | Me | n-Bu | 95 | 5 | 224 | 172 | 148 |
| 40 | Me | n-Bu | 70 | 30 | 242 | 168 | 171 |
| 41 | Me | n-Bu | 30 | 70 | 231 | 169 | 148 |
| 42 | Me | n-Bu | 10 | 90 | 214 | 185 | 159 |
| 43 | OMe | OEt | 95 | 5 | 183 | 178 | 169 |
| 44 | OMe | OEt | 70 | 30 | 189 | 181 | 172 |
| 45 | OMe | OEt | 30 | 70 | 198 | 183 | 173 |
| 46 | OMe | OEt | 10 | 90 | 181 | 179 | 170 |
| 47 | OMe | OEt | 5 | 95 | 175 | 174 | 168 |
| 48 | Me | O benzyl | 95 | 5 | 193 | 171 | 177 |
| 49 | Me | O benzyl | 70 | 30 | 187 | 168 | 174 |
| 50 | Me | O benzyl | 30 | 70 | 181 | 164 | 173 |
| 51 | Me | O benzyl | 10 | 90 | 179 | 162 | 170 |
| 52 | Me | O benzyl | 5 | 95 | 173 | 161 | 168 |
| 53 | n-Bu | NMe2 | 95 | 5 | 201 | 183 | 160 |
| 54 | n-Bu | NMe2 | 70 | 30 | 199 | 182 | 161 |
| 55 | n-Bu | NMe2 | 30 | 70 | 209 | 170 | 155 |
| 56 | n-Bu | NMe2 | 10 | 90 | 198 | 176 | 157 |
| 57 | n-Bu | NMe2 | 5 | 95 | 200 | 172 | 154 |
| 58 | H | Azide | 95 | 5 | 199 | 189 | 168 |
| 59 | H | Azide | 70 | 30 | 206 | 186 | 165 |
| 60 | H | Azide | 30 | 70 | 211 | 182 | 162 |
| 61 | H | Azide | 10 | 90 | 219 | 179 | 160 |
| 62 | H | Azide | 5 | 95 | 209 | 170 | 159 |

Any of the adsorption amounts is measured in mL/g.
The measurement temperature of carbon dioxide is 195 K, and the measurement temperature of oxygen and nitrogen is 77 K.

TABLE 2

| Example | Functional group A | Functional group B | A content (%) | B content (%) | Carbon dioxide adsorption amount | Oxygen adsorption amount | Nitrogen adsorption amount |
|---|---|---|---|---|---|---|---|
| 63 | H | tBu | 95 | 5 | 289 | 11 | 18 |
| 64 | H | tBu | 70 | 30 | 286 | 8 | 11 |
| 65 | H | tBu | 30 | 70 | 301 | 25 | 33 |
| 66 | H | tBu | 5 | 95 | 299 | 32 | 21 |
| 67 | Me | tBu | 95 | 5 | 203 | 6 | 6 |
| 68 | Me | tBu | 70 | 30 | 231 | 10 | 8 |
| 69 | Me | tBu | 30 | 70 | 243 | 5 | 10 |
| 70 | Me | tBu | 10 | 90 | 234 | 9 | 5 |

Any of the adsorption amounts is measured in mL/g.
The measurement temperature of carbon dioxide is 195 K, and the measurement temperatures of oxygen and nitrogen are 77 K.

TABLE 3

| Example | Functional group A | Functional group B | Functional group C | A content (%) | B content (%) | C content (%) | Carbon dioxide adsorption amount | Oxygen adsorption amount | Nitrogen adsorption amount |
|---|---|---|---|---|---|---|---|---|---|
| 71 | H | Me | nBu | 90 | 5 | 5 | 222 | 169 | 189 |
| 72 | H | Me | nBu | 30 | 30 | 40 | 232 | 189 | 203 |
| 73 | H | Me | nBu | 5 | 95 | 5 | 199 | 201 | 198 |
| 74 | Me | OMe | NMe2 | 90 | 5 | 5 | 202 | 189 | 169 |
| 75 | Me | OMe | NMe2 | 30 | 30 | 40 | 189 | 194 | 172 |
| 76 | Me | OMe | NMe2 | 5 | 95 | 5 | 204 | 179 | 179 |

TABLE 4

| Comparative Example | Functional group A | Functional group B | A content (%) | B content (%) | Carbon dioxide adsorption amount | Oxygen adsorption amount | Nitrogen adsorption amount |
|---|---|---|---|---|---|---|---|
| 1 | H | Me | 100 | 0 | 170 | 43 | 42 |
| 2 | H | Me | 98 | 2 | 173 | 36 | 29 |
| 3 | H | Me | 2 | 98 | 179 | 26 | 22 |
| 4 | H | Me | 0 | 100 | 177 | 46 | 25 |
| 5 | H | n-Bu | 98 | 2 | 132 | 51 | 72 |
| 6 | H | n-Bu | 2 | 98 | 101 | 73 | 46 |
| 7 | H | n-Bu | 0 | 100 | 107 | 69 | 62 |
| 8 | H | OMe | 98 | 2 | 109 | 88 | 39 |
| 9 | H | OMe | 2 | 98 | 121 | 93 | 72 |
| 10 | H | OMe | 0 | 100 | 108 | 91 | 91 |
| 11 | H | NMe2 | 98 | 2 | 183 | 81 | 39 |
| 12 | H | NMe2 | 2 | 98 | 222 | 51 | 31 |
| 13 | H | NMe2 | 0 | 100 | 231 | 28 | 27 |
| 14 | H | OH | 98 | 2 | 142 | 68 | 71 |
| 15 | H | OH | 2 | 98 | 121 | 71 | 51 |
| 16 | H | OH | 0 | 100 | 91 | 99 | 27 |
| 17 | H | CO2H | 98 | 2 | 101 | 87 | 72 |
| 18 | H | CO2H | 2 | 98 | 108 | 69 | 59 |
| 19 | H | CO2H | 0 | 100 | 81 | 49 | 52 |
| 20 | H | SO3H | 98 | 2 | 121 | 87 | 28 |
| 21 | H | SO3H | 2 | 98 | 143 | 59 | 21 |
| 22 | H | SO3H | 0 | 100 | 155 | 64 | 53 |
| 23 | H | OMe | 98 | 2 | 121 | 78 | 74 |
| 24 | H | OMe | 2 | 98 | 102 | 79 | 48 |
| 25 | H | OMe | 0 | 100 | 95 | 94 | 67 |
| 26 | Me | OMe | 100 | 0 | 99 | 79 | 81 |
| 27 | Me | OMe | 98 | 2 | 104 | 68 | 57 |
| 28 | Me | OMe | 2 | 98 | 86 | 63 | 69 |
| 29 | Me | OMe | 0 | 100 | 79 | 63 | 86 |
| 30 | Me | n-Bu | 98 | 2 | 123 | 73 | 74 |
| 31 | Me | n-Bu | 2 | 98 | 108 | 69 | 83 |
| 32 | Me | n-Bu | 0 | 100 | 111 | 48 | 27 |
| 33 | H | tBu | 98 | 2 | 169 | 47 | 40 |
| 34 | H | tBu | 2 | 98 | 209 | 221 | 40 |
| 35 | H | tBu | 0 | 100 | 199 | 256 | 194 |
| 36 | Me | tBu | 98 | 2 | 93 | 77 | 79 |
| 37 | Me | tBu | 2 | 98 | 199 | 232 | 178 |
| 39 | Me | tBu | 0 | 100 | 199 | 256 | 194 |
| 40 | OMe | OEt | 98 | 2 | 110 | 101 | 95 |
| 41 | OMe | OEt | 2 | 98 | 107 | 98 | 93 |
| 42 | OMe | OEt | 0 | 100 | 101 | 96 | 86 |
| 43 | Me | O benzyl | 98 | 2 | 108 | 88 | 64 |
| 44 | Me | O benzyl | 2 | 98 | 100 | 83 | 79 |
| 45 | Me | O benzyl | 0 | 100 | 95 | 59 | 71 |
| 46 | n-Bu | NMe2 | 98 | 2 | 95 | 58 | 72 |
| 47 | n-Bu | NMe2 | 2 | 98 | 92 | 69 | 70 |
| 48 | H | Azide | 98 | 2 | 99 | 62 | 58 |
| 49 | H | Azide | 2 | 98 | 87 | 60 | 55 |
| 50 | H | Azide | 0 | 100 | 88 | 59 | 63 |

TABLE 5

| Comparative Example | Functional group A | Functional group B | Functional group C | A content (%) | B content (%) | C content (%) | Carbon dioxide adsorption amount | Oxygen adsorption amount | Nitrogen adsorption amount |
|---|---|---|---|---|---|---|---|---|---|
| 51 | H | Me | nBu | 96 | 2 | 2 | 165 | 49 | 32 |
| 52 | H | Me | nBu | 2 | 96 | 2 | 182 | 39 | 41 |
| 53 | H | Me | nBu | 2 | 2 | 96 | 169 | 38 | 51 |

TABLE 5-continued

| Comparative Example | Functional group A | Functional group B | Functional group C | A content (%) | B content (%) | C content (%) | Carbon dioxide adsorption amount | Oxygen adsorption amount | Nitrogen adsorption amount |
|---|---|---|---|---|---|---|---|---|---|
| 54 | Me | OMe | NMe2 | 96 | 2 | 2 | 172 | 52 | 39 |
| 55 | Me | OMe | NMe2 | 2 | 96 | 2 | 181 | 39 | 44 |
| 56 | Me | OMe | NMe2 | 2 | 2 | 96 | 163 | 44 | 34 |

Among all of Examples 2 to 76, as a result of powder X-ray analysis, the same reflection pattern as that of Example 1 was shown. From this, it was confirmed that a porous polymer metal complex having the same Kagome structure as that of Example 1 was obtained.

In addition, it was confirmed from the analysis by the single-crystal X-ray diffraction and the powder X-ray diffraction methods that the Kagome structure was not in an interpenetration state.

In Comparative Examples 1 to 56, it was confirmed that porous polymer metal complexes having a so-called Kagome structure as in Example 1 were obtained. However, the amount of a ligand was less than 5% or more than 95%.

As can be seen from the results of Examples 1 to 62 and Comparative Examples 1 to 50, it can be seen that when the mixing ratio of two types of ligands was in a range of 5:95 to 95:5, the adsorption amount of each of gases, particularly, oxygen and nitrogen was increased compared to the porous polymer metal complex synthesized by singly using the ligands, and thus the porous polymer metal complexes could be appropriately used as a gas occlusion agent.

In addition, as can be seen from Examples 63 to 70 and Comparative Examples 33 to 39, in a case where one type of two types of ligands which were mixed was 5-tert-butylisophthalic acid and the mixing ratio of 5-tert-butylisophthalic acid was 5% or higher and 95% or lower, the adsorption amount of carbon dioxide was not significantly changed, but the adsorption amounts of oxygen and nitrogen were significantly reduced. Accordingly, it was seen that the porous polymer metal complexes could be appropriately used as a gas separation material capable of selectively trap only a single type of gas.

In addition, as can be seen from Examples 71 to 76 of Table 3 and Comparative Examples 51 to 56 of Table 5, the same tendency could be seen even in a case of mixing three types of ligands.

<Result of Gas Adsorption>

The carbon monoxide adsorption properties of the obtained gas adsorbents at 273 K were examined. For measurement, a BET automatic adsorption device (BEL-SORP-mini II manufactured by BEL Japan, Inc.) was used. Before the measurement, by drying a sample under vacuum at 393 K for 12 hours, even a small amount of solvent particles and the like that might remain were removed. The unit of the gas adsorption amount is mL/g (STP).

The results of Examples 1 to 76 are shown in Table 6.

TABLE 6

| Example | Carbon monoxide adsorption amount |
|---|---|
| 1 | 14 |
| 2 | 16 |
| 3 | 13 |
| 4 | 21 |
| 5 | 23 |
| 6 | 16 |
| 7 | 17 |
| 8 | 14 |
| 9 | 19 |
| 10 | 14 |
| 11 | 26 |
| 12 | 17 |
| 13 | 17 |
| 14 | 18 |
| 15 | 13 |
| 16 | 18 |
| 17 | 18 |
| 18 | 14 |
| 19 | 18 |
| 20 | 23 |
| 21 | 25 |
| 22 | 22 |
| 23 | 21 |
| 24 | 18 |
| 25 | 18 |
| 26 | 19 |
| 27 | 17 |
| 28 | 18 |
| 29 | 15 |
| 30 | 17 |
| 31 | 19 |
| 32 | 14 |
| 33 | 17 |
| 34 | 17 |
| 35 | 15 |
| 36 | 18 |
| 37 | 18 |
| 38 | 14 |
| 39 | 15 |
| 40 | 18 |
| 41 | 21 |
| 42 | 20 |
| 43 | 20 |
| 44 | 21 |
| 45 | 24 |
| 46 | 17 |
| 47 | 18 |
| 48 | 19 |
| 49 | 15 |
| 50 | 17 |
| 51 | 15 |
| 52 | 18 |
| 53 | 15 |
| 54 | 19 |
| 55 | 18 |
| 56 | 18 |
| 57 | 17 |
| 58 | 16 |
| 59 | 19 |
| 60 | 19 |
| 61 | 16 |
| 62 | 17 |
| 63 | 16 |
| 64 | 20 |
| 65 | 18 |
| 66 | 18 |
| 67 | 19 |
| 68 | 26 |
| 69 | 27 |
| 70 | 18 |
| 71 | 26 |
| 72 | 24 |

TABLE 6-continued

| Example | Carbon monoxide adsorption amount |
|---|---|
| 73 | 18 |
| 74 | 17 |
| 75 | 18 |
| 76 | 15 |

The results of Comparative Examples 1 to 56 are shown in Table 7.

TABLE 7

| Comparative Example | Carbon monoxide adsorption amount | Comparative Example | Carbon monoxide adsorption amount |
|---|---|---|---|
| 1 | 3 | 28 | 4 |
| 2 | 4 | 29 | 4 |
| 3 | 1 | 30 | 3 |
| 4 | 4 | 31 | 4 |
| 5 | 2 | 32 | 2 |
| 6 | 3 | 33 | 3 |
| 7 | 4 | 34 | 2 |
| 8 | 2 | 35 | 3 |
| 9 | 3 | 36 | 3 |
| 10 | 1 | 37 | 4 |
| 11 | 4 | 38 | 4 |
| 12 | 3 | 39 | 2 |
| 13 | 2 | 40 | 2 |
| 14 | 4 | 41 | 1 |
| 15 | 2 | 42 | 4 |
| 16 | 3 | 43 | 2 |
| 17 | 4 | 44 | 3 |
| 18 | 1 | 45 | 2 |
| 19 | 5 | 46 | 3 |
| 20 | 3 | 47 | 1 |
| 21 | 2 | 48 | 3 |
| 22 | 3 | 49 | 2 |
| 23 | 3 | 50 | 2 |
| 24 | 2 | 51 | 3 |
| 25 | 4 | 52 | 2 |
| 26 | 2 | 53 | 4 |
| 27 | 4 | 54 | 1 |
| 28 | 4 | 55 | 2 |
| 29 | 4 | 56 | 1 |

From the results, it can be seen that all the materials obtained in Examples had excellent carbon monoxide adsorption properties.

Example 77

Water (2 mL) in which 0.02 mmol of copper nitrate trihydrate was dissolved and water (2 mL) in which 0.02 mmol of 5-(N,N-dimethylamino)isophthalic acid and 0.04 mmol of lithium hydroxide were dissolved were slowly stacked, and the resultant was left for 72 hours, thereby obtaining a hexagonal-plate-shaped light blue single crystal. After the single crystal having a diameter of about 250 μm was coated with Paratone so as not to be exposed to the air, a crystal diffraction image was obtained by a single-crystal measurement device manufactured by Rigaku Corporation (single-crystal structural analysis device for very small crystals, VariMax, MoKα radiation ($\lambda$=0.71069 Å), an irradiation time of 12 seconds, d=45 mm, 2θ=−20 degrees, a temperature of −180° C.), the obtained diffraction image was analyzed by using an analysis software "Yadokari XG2009", and it was confirmed that the single crystal had a Kagome structure illustrated in FIG. 4 (a=12.8, b=18.504, c=6.7249; α=90, β=90, γ=120; space group=P321).

In addition, 1 mmol of copper nitrate trihydrate and 1 mmol of 5-(N,N-dimethylamino)isophthalic acid were dispersed in methanol (20 mL), 2 mmol of pyridine was added thereto, the container was sealed, and then the resultant was heated at 120° C. for 1 hour. After cooling, the resultant was filtered and washed with methanol, thereby obtaining 129 mg of blue powder. As a result of measuring the powder by using a powder X-ray device DISCOVER D8 with GADDS manufactured by Bruker AXS K.K. (CuKα ($\lambda$=1.54 Å), 2θ=4 to 40 degrees, measured at room temperature), reflections occurred at 5.6 degrees, 9.6 degrees, 11.0 degrees, 12.8 degrees, 14.0 degrees, 16.5 degrees, and 17.0 degrees (FIG. 5). The reflections were the same as those in the powder simulation pattern of the single crystal. That is, it was confirmed that the porous polymer metal complex having a Kagome structure could be synthesized by the above-described two methods and the porous polymer metal complex could be analyzed by the single-crystal X-ray diffraction and the powder X-ray diffraction methods.

Comparative Example 57

A porous polymer metal complex having a Kagome structure having an amino group at position 5 of isophthalic acid was synthesized in the same manner as that of Example 1, <Result of Gas Adsorption>

The adsorption properties of the obtained gas adsorbent for various gases were measured at various temperatures. A BET automatic adsorption device (BELSORP-mini II manufactured by BEL Japan, Inc.) was used. Before the measurement, by drying a sample under vacuum at 393 K for 6 hours, even a small amount of solvent particles and the like that might remain were removed.

Examples 78 to 84

Various porous polymer metal complexes having a Kagome structure having an amino group at position 5 of isophthalic acid, which are shown in Table 8, were synthesized in the same manner as that of Example 77. Among all of the porous polymer metal complexes, as a result of powder X-ray analysis, the same reflection pattern as described above was obtained. From this, it was confirmed that the porous polymer metal complexes had a Kagome structure.

In Tables 8 and 9, the adsorption amounts of various gases at various temperatures are shown. In addition, in all of Tables 8 to 11, the adsorption amount is an adsorption amount at a relative pressure of 0.95, and the relative pressure is a value obtained by dividing a pressure during adsorption by the boiling point of a corresponding gas at a corresponding temperature.

At any temperature, the porous polymer metal complex of the present invention which used an isophthalic acid having a substituted amino group at position 5 trapped a large amount of only carbon dioxide gas, and the adsorption amounts of other gases were significantly small. The effect is obvious when the porous polymer metal complex is compared to the porous polymer metal complex of Comparative Example 57 which used an isophthalic acid having an unsubstituted amino group at position 5.

TABLE 8

| Example | Functional group | Carbon dioxide*1 | Nitrogen*2 | Oxygen*2 | Methane*3 | Carbon dioxide*4 | Nitrogen*4 | Oxygen*4 | Methane*4 |
|---|---|---|---|---|---|---|---|---|---|
| 77 | Dimethylamino | 231 | 27 | 28 | 14 | 29 | 4 | 4 | 3 |
| 78 | Methylamino | 129 | 5 | 7 | 32 | 37 | 4 | 3 | 3 |
| 79 | Diethylamino | 119 | 6 | 5 | 15 | 26 | 3 | 3 | 2 |
| 80 | Ethylamino | 104 | 3 | 6 | 29 | 24 | 4 | 3 | 2 |
| 81 | Dibutylamino | 109 | 7 | 5 | 31 | 27 | 3 | 2 | 3 |
| 82 | Methylethylamino | 111 | 4 | 6 | 32 | 22 | 5 | 2 | 4 |
| 83 | 5-pyrrolidine-1-yl | 145 | 9 | 5 | 29 | 33 | 2 | 3 | 3 |
| 84 | Phenylamino | 72 | 3 | 5 | 27 | 23 | 2 | 1 | 2 |

*1 Gas adsorption amount at 195 K
*2 Gas adsorption amount at 77 K
*3 Gas adsorption amount at 91 K
*4 Gas adsorption amount at 273 K
The adsorption amount is an adsorption amount at a relative pressure (note) of 0.95.
The relative pressure is a value obtained by dividing a pressure during adsorption by the boiling point of a corresponding gas at a corresponding temperature.

TABLE 9

| Comparative Example | Ligand | Carbon dioxide*1 | Nitrogen*2 | Oxygen*2 | Methane*3 | Carbon dioxide*4 | Nitrogen*4 | Oxygen*4 | Methane*4 |
|---|---|---|---|---|---|---|---|---|---|
| 57 | Unsubstituted amino | 36 | 18 | 17 | 14 | 8 | 3 | 4 | 5 |

*1 Gas adsorption amount at 195 K
*2 Gas adsorption amount at 77 K
*3 Gas adsorption amount at 91 K
*4 Gas adsorption amount at 273 K

Examples 85 to 88 and Comparative Examples 58 to 60

The results of a case where an isophthalic acid (ligand B) was added to a 5-N,N-dimethylamino isophthalic acid ligand (ligand A) to be mixed and used as the raw material in the same manner as that of Example 77 are shown in Example 85 to 88 and Comparative Examples 58 to 60. In addition, it was confirmed from analysis by the single-crystal X-ray diffraction and the powder X-ray diffraction methods that the Kagome structure was not in an interpenetration state.

Even in a case where the 5-N,N-dimethylamino isophthalic acid ligand was mixed for use at a ratio of 5% or higher, the same effect as that of Example 77 was obtained.

TABLE 10

| Example | Ligand A (here, ligand B is isophthalic acid) | Ligand A content (%) | Ligand B content (%) | Carbon dioxide*1 | Nitrogen*2 | Oxygen*2 | Methane*3 | Carbon dioxide*4 | Nitrogen*4 | Oxygen*4 | Methane*4 |
|---|---|---|---|---|---|---|---|---|---|---|---|
| 85 | Dimethylamino | 80 | 20 | 222 | 8 | 15 | 14 | 29 | 4 | 4 | 3 |
| 86 | Dimethylamino | 50 | 50 | 210 | 13 | 22 | 12 | 30 | 4 | 3 | 3 |
| 87 | Dimethylamino | 20 | 80 | 208 | 21 | 21 | 18 | 28 | 4 | 4 | 3 |
| 88 | Dimethylamino | 5 | 95 | 185 | 13 | 24 | 38 | 20 | 3 | 3 | 2 |

*1 Gas adsorption amount at 195 K
*2 Gas adsorption amount at 77 K
*3 Gas adsorption amount at 91 K
*4 Gas adsorption amount at 273 K

TABLE 11

| Comparative Example | Ligand A (here, ligand B is isophthalic acid) | Ligand A content (%) | Ligand B content (%) | Carbon dioxide*1 | Nitrogen*2 | Oxygen*2 | Methane*3 | Carbon dioxide*4 | Nitrogen*4 | Oxygen*4 | Methane*4 |
|---|---|---|---|---|---|---|---|---|---|---|---|
| 58 | Dimethylamino | 4 | 96 | 205 | 46 | 38 | 79 | 14 | 3 | 2 | 3 |
| 59 | Dimethylamino | 2 | 98 | 198 | 41 | 31 | 89 | 12 | 3 | 4 | 4 |
| 60 | Dimethylamino | 0 | 100 | 177 | 25 | 46 | 102 | 11 | 3 | 3 | 4 |

*1 Gas adsorption amount at 195 K
*2 Gas adsorption amount at 77 K
*3 Gas adsorption amount at 91 K
*4 Gas adsorption amount at 273 K

Examples 89 to 93

Porous polymer metal complexes having a Kagome structure shown in Table 12 were synthesized by mixing a 5-N,N-dimethylamino isophthalic acid ligand with a 5-n-butyl-isophthalic acid ligand and using as the raw material in the same manner as that of Example 77. As a result of powder X-ray analysis, the same reflection pattern as described above was obtained. From this, it was confirmed that the porous polymer metal complexes had a Kagome structure. In addition, it was confirmed from analysis by the single-crystal X-ray diffraction and the powder X-ray diffraction methods that the Kagome structure was not in an interpenetration state.

Results of evaluating the gas adsorption amounts of the obtained porous polymer metal complexes in the same manner as that of Example 77 are shown in Table 12.

diffraction image was obtained by a single-crystal measurement device manufactured by Rigaku Corporation (single-crystal structural analysis device for very small crystals, VariMax, MoKα radiation ($\lambda$=0.71069 Å), an irradiation time of 4 seconds, d=45 mm, 2θ=−20 degrees, a temperature of −180° C.), the obtained diffraction image was analyzed by using an analysis software "Yadokari XG2009", and it was confirmed that the single crystal had a Kagome structure illustrated in FIG. 1 (a=18.504, b=18.504, c=6.7249; α=90, β=90, γ=120; space group=P321).

In addition, 1 mmol of copper nitrate trihydrate and 1 mmol of 5-tert-butylisophthalic acid were dispersed in methanol (20 mL), 2 mmol of pyridine was added thereto, the container was sealed, and then the resultant was heated at 120° C. for 1 hour. After cooling, the reaction mixture was shaken and was thereafter subjected to centrifugation by a centrifuge at 1000 revolutions for two minutes, and the

TABLE 12

| Example | Functional group A | Functional group B | A content (%) | B content (%) | Carbon dioxide adsorption amount | Oxygen adsorption amount | Nitrogen adsorption amount |
|---|---|---|---|---|---|---|---|
| 89 | NMe2 | n-Bu | 5 | 95 | 201 | 183 | 160 |
| 90 | NMe2 | n-Bu | 30 | 70 | 199 | 182 | 161 |
| 91 | NMe2 | n-Bu | 70 | 30 | 209 | 170 | 155 |
| 92 | NMe2 | n-Bu | 90 | 10 | 198 | 176 | 157 |
| 93 | NMe2 | n-Bu | 95 | 5 | 200 | 172 | 154 |

Any of the adsorption amounts is measured in mL/g.
The measurement temperature of carbon dioxide is 195 K, and the measurement temperatures of oxygen and nitrogen are 77 K.

Examples 94 to 96

Porous polymer metal complexes having a Kagome structure shown in Table 13 were synthesized by mixing a 5-N,N-dimethylamino isophthalic acid ligand (ligand A), a 5-methylisophthalic acid ligand (ligand B), and a 5-methoxyisophthalic acid ligand (ligand C) with each other and using as the raw material in the same manner as that of Example 77. As a result of powder X-ray analysis, the same reflection pattern as described above was obtained. From this, it was confirmed that the porous polymer metal complexes had a Kagome structure. In addition, it was confirmed from analysis by the single-crystal X-ray diffraction and the powder X-ray diffraction methods that the Kagome structure was not in an interpenetration state.

Figure 10:
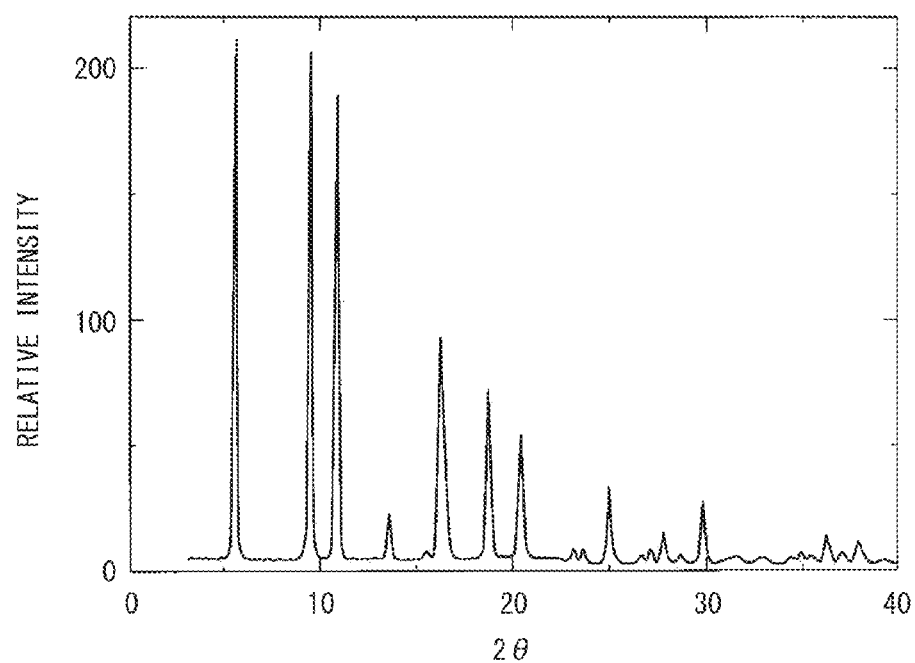
FIG. 10 illustrates an X-ray diffraction pattern of a result obtained by measuring a powder (in a case where a functional group at position 5 is a tBu group) obtained in Example 97 using a powder X-ray device.

Results of evaluating the gas adsorption amounts of the obtained porous polymer metal complexes in the same manner as that of Example 77 are shown in Table 13.

supernatant was removed. Methanol was added to the residue, the resultant was re-filtered and was subjected to centrifugation by a centrifuge at 1000 revolutions for two minutes, and the supernatant was removed. The residue was dispersed in methanol, and the resultant was filtered and washed with methanol, thereby obtaining 67 mg of blue powder. As a result of measuring the powder by using a powder X-ray device DISCOVER D8 with GADDS manufactured by Bruker AXS K.K. (CuKα ($\lambda$=1.54 Å), 2θ=4 to 40 degrees, measured at room temperature), reflections occurred at 5.6 degrees, 9.6 degrees, 11.0 degrees, 12.8 degrees, 14.0 degrees, 16.5 degrees, and 17.0 degrees (FIG. 10). The reflections were the same as those in the powder simulation pattern of the single crystal. That is, it was confirmed that the porous polymer metal complex having a Kagome structure could be synthesized by the above-described two methods and the porous polymer metal complex

TABLE 13

| Example | Functional group A | Functional group B | Functional group C | A content (%) | B content (%) | C content (%) | Carbon dioxide adsorption amount | Oxygen adsorption amount | Nitrogen adsorption amount |
|---|---|---|---|---|---|---|---|---|---|
| 94 | NMe2 | Me | OMe | 5 | 90 | 5 | 202 | 189 | 169 |
| 95 | NMe2 | Me | OMe | 40 | 30 | 30 | 189 | 194 | 172 |
| 96 | NMe2 | Me | OMe | 5 | 5 | 95 | 204 | 179 | 179 |

Example 97

Water (2 mL) in which 0.02 mmol of copper nitrate trihydrate was dissolved and water (2 mL) in which 0.02 mmol of 5-tert-butylisophthalic acid and 0.04 mmol of lithium hydroxide were dissolved were slowly stacked, and the resultant was left for 72 hours, thereby obtaining a hexagonal-plate-shaped light blue single crystal. After the single crystal having a diameter of about 80 μm was coated with Paratone so as not to be exposed to the air, a crystal could be analyzed by the single-crystal X-ray diffraction and the powder X-ray diffraction method.

Although the present material is a porous polymer metal complex and an infinite chain body, FIG. 9A illustrates only two layers extracted and drawn from the side surface. It can be seen that in a case where the substituent at position 5 is t-Bu, the tBu groups collide with each other between the layers and thus the distance between the layers is large compared to a case where the substituent at position 5 is a methyl group (Me) which is smaller than t-Bu. In addition, t-Bu has two ways of protruding between the layers, and it can be seen that many voids are present in a part where t-Bu groups do not collide with each other. Only two layers extracted and drawn from the upper surface are illustrated in FIG. 2. In a case of t-Bu, a stacking manner is completely different from that in a case of Me (FIG. 9B), and thus it can be seen that while pores having relatively simple shapes are formed in a case of Me, complex pores are formed in a case of t-Bu because molecules protrude and thus a complex pore structure is formed.

Examples 98 to 110

Various porous polymer metal complexes having a Kagome structure shown in Table 14, which are formed from isophthalic acid derivative ions having a branched alkyl group or a branched alkoxy group at position 5 were synthesized in the same manner as that of Example 97. Among all of the porous polymer metal complexes, as a result of powder X-ray analysis, the same reflection pattern as described above was shown. From this, it was confirmed that the porous polymer metal complexes had a Kagome structure.

<Result of Gas Adsorption>

The adsorption properties of the obtained gas adsorbent for various gases were measured at various temperatures. A BET automatic adsorption device (BELSORP-mini II manufactured by BEL Japan, Inc.) was used. Before the measurement, by drying a sample under vacuum at 393 K for 6 hours, even a small amount of solvent particles and the like that might remain were removed.

For various porous polymer metal complexes of Examples 97 to 110, the oxygen gas adsorption amounts at 77 K are shown in Table 14, the nitrogen monoxide gas adsorption amounts at 121 K are shown in Table 15, and the carbon dioxide gas adsorption amounts at 195 K are shown in Table 16. In all of Tables 14 to 16, the adsorption amount is an adsorption amount at a relative pressure of 0.95, and the relative pressure is a value obtained by dividing a pressure during adsorption by the boiling point of a corresponding gas at a corresponding temperature.

TABLE 14

Oxygen gas adsorption amount at 77 K

| Example | Substituent at position 5 | Adsorption amount (mL/g) |
|---|---|---|
| 97 | Isopropyl | 222 |
| 98 | Isobutyl | 245 |
| 99 | Tert-butyl | 262 |
| 100 | 2-pentyl | 231 |
| 101 | 3-pentyl | 217 |
| 102 | 2-hexyl | 232 |
| 103 | 3-hexyl | 215 |
| 104 | Isopropyloxy | 201 |
| 105 | Isobutyloxy | 231 |
| 106 | Tert-butyloxy | 215 |
| 107 | 2-pentyloxy | 218 |
| 108 | 3-pentyloxy | 224 |
| 109 | 2-hexyloxy | 217 |
| 110 | 3-hexyloxy | 216 |

The adsorption amount is an adsorption amount at a relative pressure (note) of 0.95.
The relative pressure is a value obtained by dividing a pressure during adsorption by the boiling point of a corresponding gas at a corresponding temperature.

TABLE 15

Nitrogen monoxide gas adsorption amount at 121 K

| Example | Substituent at position 5 | Adsorption amount (mL/g) |
|---|---|---|
| 97 | Isopropyl | 279 |
| 98 | Isobutyl | 301 |
| 99 | Tert-butyl | 359 |
| 100 | 2-pentyl | 338 |
| 101 | 3-pentyl | 317 |
| 102 | 2-hexyl | 298 |
| 103 | 3-hexyl | 279 |
| 104 | Isopropyloxy | 291 |
| 105 | Isobutyloxy | 332 |
| 106 | Tert-butyloxy | 319 |
| 107 | 2-pentyloxy | 299 |
| 108 | 3-pentyloxy | 301 |
| 109 | 2-hexyloxy | 298 |
| 110 | 3-hexyloxy | 311 |

TABLE 16

Carbon dioxide gas adsorption amount at 195 K

| Example | Substituent at position 5 | Adsorption amount (mL/g) |
|---|---|---|
| 97 | Isopropyl | 201 |
| 98 | Isobutyl | 221 |
| 99 | Tert-butyl | 232 |
| 100 | 2-pentyl | 197 |
| 101 | 3-pentyl | 200 |
| 102 | 2-hexyl | 189 |
| 103 | 3-hexyl | 195 |
| 104 | Isopropyloxy | 221 |
| 105 | Isobutyloxy | 202 |
| 106 | Tert-butyloxy | 204 |
| 107 | 2-pentyloxy | 199 |
| 108 | 3-pentyloxy | 221 |
| 109 | 2-hexyloxy | 206 |
| 110 | 3-hexyloxy | 197 |

Comparative Examples 61 to 66

As Comparative Examples 61 to 66, isophthalic acid derivatives in which an isophthalic acid had a functional group shown in Table 17, which did not have a branched structure, at position 5 were synthesized by using Frieda-Crafts Alkylation reaction and the like, and porous polymer metal complexes were synthesized by using the resultant. Among all of the porous polymer metal complexes, as a result of powder X-ray analysis, the same reflection pattern as described above was shown. From this, it was confirmed that the porous polymer metal complexes had a Kagome structure.

For the porous polymer metal complexes produced in Comparative Examples 61 to 66, gas adsorption amounts were evaluated in the same manner as those of Examples 97 to 110, and the results are shown in Tables 17 to 19. Table 17 shows the oxygen gas adsorption amounts at 77 K, Table 18 shows the nitrogen monoxide gas adsorption amounts at 121 K, and Table 19 shows the carbon dioxide gas adsorption amounts at 195 K. In all of Tables 17 to 19, the adsorption amount is an adsorption amount at a relative pressure of 0.95, and the relative pressure is a value obtained by dividing a pressure during adsorption by the boiling point of a corresponding gas at a corresponding temperature.

TABLE 17

Oxygen gas adsorption amount at 77 K

| Comparative Example | Substituent at position 5 | Adsorption amount (mL/g) |
|---|---|---|
| 61 | n-propyl | 35 |
| 62 | n-butyl | 24 |
| 63 | n-hexyl | 46 |
| 64 | n-propyloxy | 43 |
| 65 | n-butyloxy | 31 |
| 66 | n-hexyloxy | 51 |

TABLE 18

Nitrogen monoxide gas adsorption amount at 121 K

| Comparative Example | Substituent at position 5 | Adsorption amount (mL/g) |
|---|---|---|
| 61 | n-propyl | 23 |
| 62 | n-butyl | 31 |
| 63 | n-hexyl | 36 |
| 64 | n-propyloxy | 26 |
| 65 | n-butyloxy | 29 |
| 66 | n-hexyloxy | 33 |

TABLE 19

Carbon dioxide gas adsorption amount at 195 K

| Comparative Example | Substituent at position 5 | Adsorption amount (mL/g) |
|---|---|---|
| 61 | n-propyl | 31 |
| 62 | n-butyl | 23 |
| 63 | n-hexyl | 36 |
| 64 | n-propyloxy | 21 |
| 65 | n-butyloxy | 24 |
| 66 | n-hexyloxy | 24 |

Examples 111 to 114 and Comparative Examples 67 to 69

As Examples 111 to 114 and Comparative Examples 67 to 69, solid solution type porous polymer metal complexes were produced by using a mixture of an isophthalic acid (ligand B) and a 5-tert-butylisophthalic acid ligand (ligand A) as the raw material. Among all of the porous polymer metal complexes, as a result of powder X-ray analysis, the same reflection pattern as described above was obtained. From this, it was confirmed that the porous polymer metal complexes had a Kagome structure. In addition, it was confirmed from analysis by the single-crystal X-ray diffraction and the powder X-ray diffraction methods that the Kagome structure was not in an interpenetration state.

A result of measuring various gas adsorption amounts for the solid solution type porous polymer metal complexes is shown in Tables 20 to 22 and Tables 23 to 25. In all of Tables 20 to 25, the adsorption amount is an adsorption amount at a relative pressure of 0.95, and the relative pressure is a value obtained by dividing a pressure during adsorption by the boiling point of a corresponding gas at a corresponding temperature.

In a case where the 5-tert-butylisophthalic acid ligand was used in the mixture at a ratio of 5% or higher, the same effect as that of Example 97 was exhibited.

TABLE 20

Oxygen gas adsorption amount at 77 K

| Example | Ligand A content (%) | Ligand B content (%) | Adsorption amount (mL/g) |
|---|---|---|---|
| 111 | 80 | 20 | 263 |
| 112 | 50 | 50 | 259 |
| 113 | 20 | 80 | 248 |
| 114 | 5 | 95 | 238 |

TABLE 21

Nitrogen monoxide gas adsorption amount at 121 K

| Example | Ligand A content (%) | Ligand B content (%) | Adsorption amount (mL/g) |
|---|---|---|---|
| 111 | 80 | 20 | 347 |
| 112 | 50 | 50 | 339 |
| 113 | 20 | 80 | 321 |
| 114 | 5 | 95 | 289 |

TABLE 22

Carbon dioxide gas adsorption amount at 195 K

| Example | Ligand A content (%) | Ligand B content (%) | Adsorption amount (mL/g) |
|---|---|---|---|
| 111 | 80 | 20 | 222 |
| 112 | 50 | 50 | 207 |
| 113 | 20 | 80 | 199 |
| 114 | 5 | 95 | 203 |

TABLE 23

Oxygen gas adsorption amount at 77 K

| Comparative Example | Ligand A content (%) | Ligand B content (%) | Adsorption amount (mL/g) |
|---|---|---|---|
| 67 | 4 | 96 | 121 |
| 68 | 2 | 98 | 78 |
| 69 | 0 | 100 | 61 |

TABLE 24

Nitrogen monoxide gas adsorption amount at 121 K

| Comparative Example | Ligand A content (%) | Ligand B content (%) | Adsorption amount (mL/g) |
|---|---|---|---|
| 67 | 4 | 96 | 71 |
| 68 | 2 | 98 | 32 |
| 69 | 0 | 100 | 18 |

TABLE 25

Carbon dioxide gas adsorption amount at 195 K

| Comparative Example | Ligand A content (%) | Ligand B content (%) | Adsorption amount (mL/g) |
|---|---|---|---|
| 67 | 4 | 96 | 69 |
| 68 | 2 | 98 | 51 |
| 69 | 0 | 100 | 38 |

Examples 115 to 118

Porous polymer metal complexes having a Kagome structure were synthesized by using a mixture of a 5-tert-butylisophthalic acid ligand and an isophthalic acid ligand having a methyl group at position 5 as the raw material in the same manner as that of Example 111. As a result of powder X-ray analysis, the same reflection pattern as described above was obtained. From this, it was confirmed that the porous polymer metal complexes had a Kagome structure. In addition, it was confirmed from analysis by the single-crystal X-ray diffraction and the powder X-ray diffraction methods that the Kagome structure was not in an interpenetration state.

The results of the gas adsorption amounts of the obtained porous polymer metal complexes are shown in Table 26.

TABLE 26

| Example | Functional group A | Functional group B | A content (%) | B content (%) | Carbon dioxide adsorption amount | Oxygen adsorption amount | Nitrogen adsorption amount |
|---|---|---|---|---|---|---|---|
| 115 | tBu | Me | 5 | 95 | 203 | 6 | 6 |
| 116 | tBu | Me | 30 | 70 | 231 | 10 | 8 |
| 117 | tBu | Me | 70 | 30 | 243 | 5 | 10 |
| 118 | tBu | Me | 90 | 10 | 234 | 9 | 5 |

Any of the adsorption amounts is measured in mL/g.
The measurement temperature of carbon dioxide is 195 K, and the measurement temperatures of oxygen and nitrogen are 77 K.

Regarding any of the gases, it was found that a material having a branched alkyl group or a branched alkoxy group at position 5 has excellent gas adsorption capacity compared to a material having an unbranched alkyl group and an unbranched alkoxy group at position 5.

The Kagome type porous polymer metal complex has, as illustrated in FIGS. 1 to 3, a network structure formed by a combination of large hexagons and small triangles formed with a paddle-wheel structure as the apex. Here, the skeleton of isophthalic acid itself forms the network structure, and the substituent itself at position 5 does not participate in the network formation. That is, regardless of a substituent at position 5, the size of the basic structure of the Kagome network is the same.

Therefore, generally, it is assumed that when the substituent at position 5 is large, the porosity is reduced and thus the gas adsorption amount is reduced due to the volume occupied by the substituent. However, actually, as shown in Tables 1 and 2, it can be seen that the size (occupied volume) of a functional group hardly affects the gas adsorption amount, and the gas adsorption amount depends on whether the structure is a linear structure or a branched structure. It is thought that this is because an alkyl group having a branched structure or a branched alkoxy group is rigid and has a large volume compared to an alkyl group or alkoxy group having a linear structure, and the groups collide with each other. Therefore, a phenomenon occurs whereby the distance between layers of a Kagome skeleton increases, and consequently, the porosity is increased, resulting in an increase in the gas occlusion amount. An effect of increasing the adsorption amount due to the phenomenon in which the distance between layers is increased due to the molecular rigidity was unknown in the past.

Reference Examples 1 to 3

Porous polymer metal complexes having a Kagome structure were synthesized by using a mixture of an isophthalic acid ligand, a 5-methylisophthalic acid ligand, and a 5-n-butylisophthalic acid ligand with each other for use as the raw material in the same manner as that of Example 97. As a result of powder X-ray analysis, the same reflection pattern as described above was obtained. From this, it was confirmed that the porous polymer metal complexes had a Kagome structure. In addition, it was confirmed from analysis by the single-crystal X-ray diffraction and the powder X-ray diffraction methods that the Kagome structure was not in an interpenetration state.

For the obtained porous polymer metal complexes, results of evaluating the gas adsorption amounts in the same manner as that of Example 971 are shown in Table 27.

Reference Examples 4 to 6

Porous polymer metal complexes having a Kagome structure were synthesized by using a mixture of a 5-methylisophthalic acid ligand, a 5-methoxyisophthalic acid ligand, and a 5-dimethylaminoisophthalic acid ligand as the raw material in the same manner as that of Example 97. As a result of powder X-ray analysis, the same reflection pattern as described above was obtained. From this, it was confirmed that the porous polymer metal complexes had a Kagome structure.

For the obtained porous polymer metal complexes, results of evaluating the gas adsorption amounts in the same manner as that of Example 97 are shown in Table 27.

According to Reference Examples 1 to 6, along with Examples 111 to 118, it can be seen that a porous polymer metal complex having a Kagome structure can be synthesized by using a mixture of an isophthalic acid ligand or isophthalic acid ligands having various substituents at position 5 as the raw material.

TABLE 27

| Reference Example | Functional group A | Functional group B | Functional group C | A content (%) | B content (%) | C content (%) | Carbon dioxide adsorption amount | Oxygen adsorption amount | Nitrogen adsorption amount |
|---|---|---|---|---|---|---|---|---|---|
| 1 | H | Me | nBu | 90 | 5 | 5 | 222 | 169 | 189 |
| 2 | H | Me | nBu | 30 | 30 | 40 | 232 | 189 | 203 |
| 3 | H | Me | nBu | 5 | 95 | 5 | 199 | 201 | 198 |
| 4 | Me | OMe | NMe2 | 90 | 5 | 5 | 202 | 189 | 169 |
| 5 | Me | OMe | NMe2 | 30 | 30 | 40 | 189 | 194 | 172 |
| 6 | Me | OMe | NMe2 | 5 | 95 | 5 | 204 | 179 | 179 |

Example 119

Figure 11:
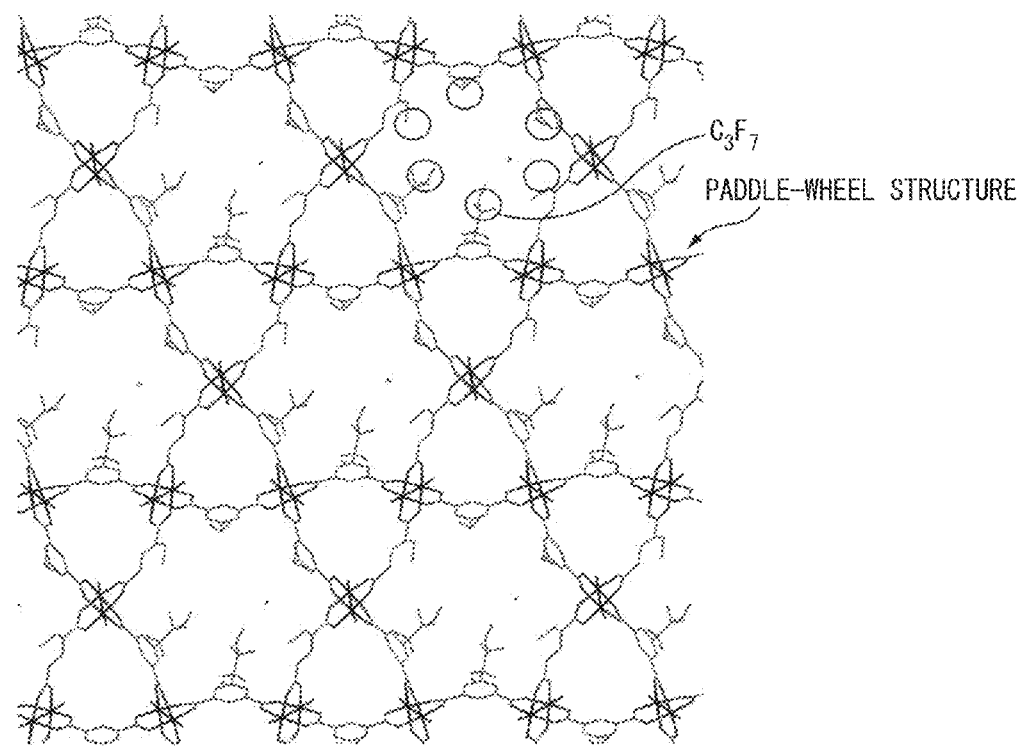
FIG. 11 illustrates a crystal structure (Kagome structure) confirmed by measuring a powder produced in Example 119 using a single-crystal measurement device (single-crystal structural analysis device for very small crystals) and analyzing the obtained diffraction image using an analysis software.

Water (2 mL) in which 0.02 mmol of copper nitrate trihydrate was dissolved and water (2 mL) in which 0.02 mmol of 5-(heptafluoro-n-propyl)isophthalic acid and 0.04 mmol of lithium hydroxide were dissolved were slowly stacked, and the resultant was left for 24 hours, thereby obtaining a hexagonal-plate-shaped light blue single crystal. After the single crystal having a diameter of about 100 μm was coated with Paratone so as not to be exposed to the air, a crystal diffraction image was obtained by a single-crystal measurement device manufactured by Rigaku Corporation (single-crystal structural analysis device for very small crystals, VariMax, MoKα radiation (λ=0.71069 Å), an irradiation time of 12 seconds, d=45 mm, 2θ=–20 degrees, a temperature of –180° C.), the obtained diffraction image was analyzed by using an analysis software "Yadokari XG2009", and thus it was confirmed that the single crystal had a Kagome structure illustrated in FIG. 11 (a=18.891, b=18.891, c=21.772; α=90, β=90, γ=120; space group=P3221).

Figure 12:
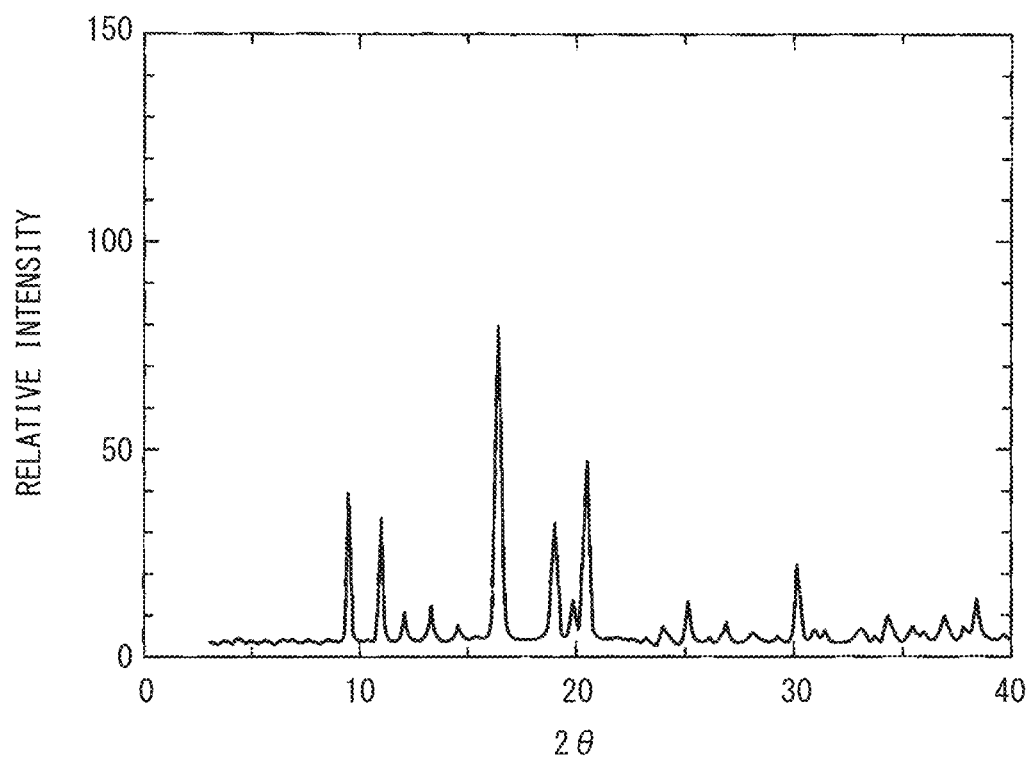
FIG. 12 illustrates a powder X-ray diffraction chart obtained by measuring the powder produced in Example 119 using the powder X-ray device.

In addition, 1 mmol of copper nitrate trihydrate and 1 mmol of 5-(heptafluoro-n-propyl)isophthalic acid were dispersed in water (20 mL), 2 mmol of pyridine was added thereto, the container was sealed, and then the resultant was heated at 150° C. for 24 hour. After cooling, the reaction mixture was shaken and was thereafter subjected to centrifugation by a centrifuge at 1000 revolutions for two minutes, and the supernatant was removed. The residue was dispersed in methanol, and the resultant was filtered through and washed with water and methanol, thereby obtaining 84 mg of blue powder. As a result of measuring the powder by using a powder X-ray device DISCOVER D8 with GADDS manufactured by Bruker AXS K.K. (CuKα (λ=1.54 Å), 2θ=4 to 40 degrees, measured at room temperature), reflections occurred at 9.42 degrees, 10.89 degrees, 12.04 degrees, 13.21 degrees, 16.27 degrees, 18.79 degrees, and 20.29 degrees (FIG. 12). The reflections were the same as those in the powder simulation pattern of the single crystal. That is, it was confirmed that the porous polymer metal complex having a Kagome structure could be synthesized by the above-described two methods and the porous polymer metal complex could be analyzed by the single-crystal X-ray diffraction and the powder X-ray diffraction methods.

Examples 120 to 128

Porous polymer metal complexes of Examples 120 to 128 shown in Table 28 were prepared by using an isophthalic acid in which position 5 was substituted by a perfluoroalkyl group or a perfluoroalkoxy group containing fluorine atoms as the ligand in the same manner as that of Example 119.

Comparative Examples 70 to 76

As Comparative Examples, porous polymer metal complexes were synthesized by using isophthalic acid derivatives in which an isophthalic acid had a functional group shown in Table 29 at position 5, in the same manner as that of Example 120.

<Result of Gas Adsorption>

The adsorption properties of the obtained gas adsorbent for various gases were measured at various temperatures. A BET automatic adsorption device (BELSORP-mini II manufactured by BEL Japan, Inc.) was used. Before the measurement, by drying a sample under vacuum at 393 K for 6 hours, even a small amount of solvent particles and the like that might remain were removed.

In Table 28, the adsorption amounts of various gases of the Kagome type porous polymer metal complexes synthesized from the isophthalic acid derivative ligand in which a perfluoroalkyl group or perfluoroalkoxy group containing 3 to 21 fluorine atoms substitutes position 5 are shown.

TABLE 28

| Examples | Substituent at position 5 | Carbon dioxide (195 K) | Nitrogen (77 K) | Oxygen (77 K) |
|---|---|---|---|---|
| 119 | CF3 | 95 | 7 | 102 |
| 120 | OCF3 | 101 | 12 | 126 |
| 121 | n-C3F7 | 125 | 13 | 173 |
| 122 | IsoC3F7 | 132 | 14 | 188 |
| 123 | n-C4F9 | 127 | 17 | 187 |
| 124 | O-n-C4F9 | 103 | 21 | 145 |
| 125 | IsoC4F9 | 131 | 12 | 179 |
| 126 | n-C5F11 | 128 | 15 | 175 |
| 127 | n-C8F17 | 134 | 16 | 152 |
| 128 | n-C10F21 | 111 | 8 | 122 |

In Table, the measurement temperature is in parentheses. All of the adsorption amounts are adsorption amounts at a relative pressure of 0.95.

In all cases, it was found that the adsorption amount of carbon dioxide or oxygen, particularly, the adsorption amount of oxygen was large, the adsorption amount of nitrogen was small, and thus a property of being capable of separating carbon dioxide/nitrogen and oxygen/nitrogen was excellent.

In Table 29, the adsorption capacities of materials obtained from an isophthalic acid derivative containing an alkyl group or an alkoxy group which does not contain 3 to 21 fluorine atoms at position 5 and copper ions are shown. Compared to Examples, the oxygen adsorption amount was small, and selectivity of carbon dioxide/nitrogen and oxygen/nitrogen as in Examples could not be obtained.

TABLE 29

Functional group at position 5 and gas adsorption capacity: in Table, all of the adsorption amounts are adsorption amounts (mL/g) at a relative pressure of 0.95.

| Comparative Example | Substituent at position 5 | Number of fluorine atoms | Carbon dioxide (195 K) | Nitrogen (77 K) | Oxygen (77 K) |
|---|---|---|---|---|---|
| 70 | Fluorine | 1 | 49 | 39 | 44 |
| 71 | CH3 | 0 | 37 | 40 | 41 |
| 72 | n-C3H7 | 0 | 31 | 46 | 39 |
| 73 | n-C4H9 | 0 | 23 | 37 | 31 |
| 74 | n-C5H11 | 0 | 41 | 40 | 40 |
| 75 | n-C8H10 | 0 | 38 | 29 | 32 |
| 76 | n-C10H21 | 0 | 28 | 28 | 23 |

In Table, the measurement temperature is in parentheses. All of the adsorption amounts are adsorption amounts at a relative pressure of 0.95.

In all of Comparative Examples, selectivity of carbon dioxide/nitrogen and oxygen/nitrogen as in Examples could not be obtained, and thus it was confirmed that the presence of a perfluoroalkyl group or perfluoroalkoxy group containing 3 to 21 fluorine atoms at position 5 of an isophthalic acid was important.

Examples 129 to 146 and Comparative Examples 77 to 92

The result of a case where a mixture of a substituted or unsubstituted isophthalic acid (ligand B) and a fluorine-containing isophthalic acid type ligand (ligand A) at ratios shown in Table 3 are used as the raw material in the same manner as that of Example 119 are shown in Examples 129 to 146 and Comparative Examples 77 to 92. In addition, it was confirmed by the single-crystal X-ray diffraction method and the powder X-ray diffraction method that the Kagome structure was not in an interpenetration state.

Even in a case (solid solution type porous polymer metal complex) where the fluorine-containing isophthalic acid type ligand (ligand A) was used in a mixture at a ratio of 5% or more, the same effect of that of Example 119 was obtained.

TABLE 30

| Example | Ligand A | Ligand B | Ligand A content (%) | Ligand B content (%) | Gas adsorption amount (mL/g) | | |
|---|---|---|---|---|---|---|---|
| | | | | | Carbon dioxide (195 K) | Nitrogen (77 K) | Oxygen (77 K) |
| 129 | CF3 | Isophthalic acid | 95 | 5 | 97 | 6 | 112 |
| 130 | CF3 | Isophthalic acid | 50 | 50 | 102 | 11 | 101 |
| 131 | CF3 | Isophthalic acid | 5 | 95 | 108 | 14 | 100 |
| 132 | CF3 | 5-methoxyisophthalic acid | 95 | 5 | 94 | 11 | 100 |
| 133 | CF3 | 5-methoxyisophthalic acid | 50 | 50 | 96 | 14 | 99 |
| 134 | CF3 | 5-methoxyisophthalic acid | 5 | 95 | 92 | 17 | 94 |
| 135 | CF3 | 5-tert-butylisophthalic acid | 95 | 5 | 96 | 16 | 99 |
| 136 | CF3 | 5-tert-butylisophthalic acid | 50 | 50 | 92 | 17 | 93 |
| 137 | CF3 | 5-tert-butylisophthalic acid | 5 | 95 | 89 | 18 | 91 |
| 138 | n-C3F7 | Isophthalic acid | 95 | 5 | 129 | 15 | 171 |
| 139 | n-C3F7 | Isophthalic acid | 50 | 50 | 133 | 19 | 161 |
| 140 | n-C3F7 | Isophthalic acid | 5 | 95 | 140 | 28 | 159 |
| 141 | IsoC4F9 | 5-ethoxyisophthalic acid | 95 | 5 | 129 | 14 | 177 |
| 142 | IsoC4F9 | 5-ethoxyisophthalic acid | 50 | 50 | 122 | 13 | 164 |
| 143 | IsoC4F9 | 5-ethoxyisophthalic acid | 5 | 95 | 113 | 19 | 128 |
| 144 | n-C8F17 | 5-methoxyisophthalic acid | 95 | 5 | 139 | 19 | 155 |
| 145 | n-C8F17 | 5-methoxyisophthalic acid | 50 | 50 | 127 | 24 | 139 |
| 146 | n-C8F17 | 5-methoxyisophthalic acid | 5 | 95 | 111 | 21 | 126 |

TABLE 31

| Comparative Examples | Ligand A | Ligand B | Ligand A content (%) | Ligand B content (%) | Gas adsorption amount (mL/g) | | |
|---|---|---|---|---|---|---|---|
| | | | | | Carbon dioxide (195 K) | Nitrogen (77 K) | Oxygen (77 K) |
| 77 | CF3 | Isophthalic acid | 97 | 3 | 99 | 52 | 63 |
| 78 | CF3 | Isophthalic acid | 3 | 97 | 162 | 57 | 41 |
| 79 | CF3 | Isophthalic acid | 0 | 100 | 170 | 42 | 43 |
| 80 | CF3 | 5-methoxyisophthalic acid | 97 | 3 | 91 | 49 | 51 |
| 81 | CF3 | 5-methoxyisophthalic acid | 3 | 97 | 99 | 87 | 59 |
| 82 | CF3 | 5-methoxyisophthalic acid | 0 | 100 | 108 | 91 | 91 |
| 83 | CF3 | 5-tert-butylisophthalic acid | 97 | 3 | 128 | 69 | 87 |
| 84 | CF3 | 5-tert-butylisophthalic acid | 3 | 97 | 149 | 116 | 143 |
| 85 | CF3 | 5-tert-butylisophthalic acid | 0 | 100 | 232 | 117 | 262 |
| 86 | n-C3F7 | Isophthalic acid | 97 | 3 | 131 | 37 | 51 |
| 87 | n-C3F7 | Isophthalic acid | 3 | 97 | 133 | 41 | 47 |
| 88 | IsoC4F9 | 5-ethoxyisophthalic acid | 97 | 3 | 122 | 59 | 88 |
| 89 | IsoC4F9 | 5-ethoxyisophthalic acid | 3 | 97 | 121 | 69 | 81 |
| 90 | IsoC4F9 | 5-ethoxyisophthalic acid | 0 | 100 | 111 | 96 | 94 |
| 91 | n-C8F17 | 5-methoxyisophthalic acid | 97 | 3 | 111 | 73 | 102 |
| 92 | n-C8F17 | 5-methoxyisophthalic acid | 3 | 97 | 101 | 81 | 94 |

<Result of Gas Adsorption>

The adsorption properties of the obtained gas adsorbent for carbon monoxide at 273 K were examined. For the measurement, a BET automatic adsorption device (BEL-SORP-mini II manufactured by BEL Japan, Inc.) was used. Before the measurement, by drying a sample under vacuum at 393 K for 12 hours, even a small amount of solvent particles and the like that might remain were removed. The unit of the gas adsorption amount is mL/g (STP).

The results of Examples 119 to 146 are shown in Table 32, and the results of Comparative Examples 70 to 92 are shown in Table 33.

TABLE 32

| Example | Carbon monoxide adsorption amount |
|---|---|
| 119 | 37 |
| 120 | 48 |
| 121 | 43 |
| 122 | 45 |
| 123 | 36 |
| 124 | 37 |
| 125 | 44 |
| 126 | 48 |

TABLE 32-continued

| Example | Carbon monoxide adsorption amount |
|---|---|
| 127 | 45 |
| 128 | 45 |
| 129 | 48 |
| 130 | 42 |
| 131 | 39 |
| 132 | 37 |
| 133 | 45 |
| 134 | 43 |
| 135 | 44 |

TABLE 32-continued

| Example | Carbon monoxide adsorption amount |
|---|---|
| 136 | 37 |
| 137 | 49 |
| 138 | 53 |
| 139 | 58 |
| 140 | 52 |
| 141 | 48 |
| 142 | 47 |
| 143 | 43 |
| 144 | 46 |
| 145 | 48 |
| 146 | 51 |

TABLE 33

| Comparative Example | Carbon monoxide adsorption amount |
|---|---|
| 70 | 4 |
| 71 | 3 |
| 72 | 4 |
| 73 | 2 |
| 74 | 1 |
| 75 | 4 |
| 76 | 2 |
| 77 | 4 |
| 78 | 1 |
| 79 | 2 |
| 80 | 3 |
| 81 | 3 |
| 82 | 2 |
| 83 | 3 |
| 84 | 4 |
| 85 | 2 |
| 86 | 4 |
| 87 | 1 |
| 88 | 1 |
| 89 | 4 |
| 90 | 3 |
| 91 | 2 |
| 92 | 2 |

From the results, it can be seen that all the materials obtained in Examples had excellent carbon monoxide adsorption properties.

INDUSTRIAL APPLICABILITY

In the first porous polymer metal complex of the present invention, a large number of pores formed by the arrangement of ligands are present in the material. With the porous properties, the first porous polymer metal complex can be used for adsorption and removal of various materials. For example, removal of toxic substances in the air, purification of water by removal of unwanted matter such as inorganic or organic matter in water, and recovery of useful substances from the air or water by trapping the useful substances in the air or water and extracting the useful substances are possible.

Particularly, in the second and third porous polymer metal complexes of the present invention, a large number of pores formed by the arrangement of ligands are present in the material. With the porous properties, selective adsorption, separation, and storage of carbon dioxide gas are possible.

In the fourth porous polymer metal complex of the present invention, a large number of pores formed by the arrangement of ligands are present in the material. With the porous properties, the adsorption amount of carbon dioxide or oxygen, particularly, oxygen is large, the adsorption amount of nitrogen is small, and thus a property of being capable of separating carbon dioxide/nitrogen and oxygen/nitrogen is excellent. Accordingly, selective adsorption, separation, and storage of carbon dioxide and oxygen are possible.

The invention claimed is:

1. A porous polymer metal complex expressed by Formula (1):

$$[CuX]_n \qquad (1)$$

wherein, in the Formula, X represents two or more types of isophthalic acid ions selected from the group consisting of isophthalic acid ions and isophthalic acid ions having a substituent at position 5, at least an amount of one type of X is 5 mol % to 95 mol % of the total number of moles of X, and n represents an assembly number of constituent units expressed by CuX and is not particularly limited.

2. The porous polymer metal complex according to claim 1, expressed by Formula (2):

$$[CuX_{1-m}Y_m]_n \qquad (2)$$

wherein, in the Formula, each of X and Y represents isophthalic acid ions or isophthalic acid ions having a substituent at position 5, X and Y are different from each other, $0.05 \leq m \leq 0.95$ is satisfied, and n represents an assembly number of constituent units expressed by $CuX_{1-m}Y_m$ and is not particularly limited.

3. The porous polymer metal complex according to claim 1,
wherein the porous polymer metal complex has a paddle-wheel structure having vertically coordinated two units in which a copper ion is coordinated to four carboxyl groups,
the paddle-wheel structure is connected by isophthalic acid derivatives to form a Kagome structure constituted by six-membered rings and three-membered rings, and
the Kagome structure has a stacked crystal structure.

4. The porous polymer metal complex according to claim 2,
wherein X in Formula (1), or X or Y in Formula (2) represents isophthalic acid ions having a substituent at position 5, and
the substituent at position 5 is a functional group selected from the group consisting of a methyl group, an ethyl group, a methoxy group, an ethoxy group, a tert-butyl group, a benzyloxy group, a nitro group, an azido group, a carboxyl group, an amino group, and a hydroxyl group.

5. The porous polymer metal complex according to claim 2,
wherein X and Y in Formula (2) represent isophthalic acid ions having a substituent at position 5,
the substituent at position 5 of X is a functional group selected from the group consisting of a methoxy group, a tert-butyl group, and a nitro group,
the substituent at position 5 of Y is a functional group selected from the group consisting of a methyl group, an ethyl group, a methoxy group, an ethoxy group, a tert-butyl group, a benzyloxy group, a nitro group, an azido group, a carboxyl group, an amino group, and a hydroxyl group, and
X and Y are different from each other.

6. A porous polymer metal complex expressed by Formula (21):

$$[CuX]_n \qquad (21)$$

wherein, in the Formula, X represents isophthalic acid ions having a substituted amino group at position 5, and n represents an assembly number of constituent units expressed by CuX and is not particularly limited.

7. The porous polymer metal complex according to claim 6,
wherein the porous polymer metal complex has a paddle-wheel structure having vertically coordinated two units in which a copper ion is coordinated to four carboxyl groups,
the paddle-wheel structure is connected by isophthalic acid derivatives to form a Kagome structure constituted by six-membered rings and three-membered rings, and
the Kagome structure has a stacked crystal structure.

8. The porous polymer metal complex according to claim 6,
wherein the substituted amino group is an amino group substituted with an alkyl group or an aryl group.

9. The porous polymer metal complex according to claim 6,
wherein the substituted amino group is a functional group selected from the group consisting of a methylamino group, a dimethylamino group, an ethylamino group, and a diethylamino group.

10. A porous polymer metal complex expressed by Formula (24):

$$[CuX]_n \qquad (24)$$

wherein, in the Formula, X represents two or more types of isophthalic acid ions selected from the group consisting of isophthalic acid ions and isophthalic acid ions having a substituent at position 5, an amount of the isophthalic acid ions having a substituted amino group at position 5 is 5 mol % or more of X, and n represents an assembly number of constituent units expressed by CuX and is not particularly limited.

11. The porous polymer metal complex according to claim 10,
wherein X in Formula (24) represents two or more types of ions selected from the group consisting of isophthalic acid ions, isophthalic acid ions having an alkyl group at position 5, isophthalic acid ions having an alkoxy group at position 5, isophthalic acid ions having an amino group at position 5, and isophthalic acid ions having a substituted amino group at position 5, and
an amount of the isophthalic acid ions having a substituted amino group at position 5 is 5 mol % or more with respect to the total number of moles of X.

12. A porous polymer metal complex expressed by Formula (31):

$$[CuX]_n \qquad (31)$$

wherein, in the Formula, X represents isophthalic acid ions having a branched alkyl group at position 5 or isophthalic acid ions having a branched alkoxy group at position 5, and the branched alkyl group is a functional group selected from the group consisting of an isopropyl group, 2-pentyl, 3-pentyl, 2-hexyl, 3-hexyl, and an isobutyl group, and n represents an assembly number of constituent units expressed by CuX and is not particularly limited,
wherein the porous polymer metal complex has a paddle-wheel structure having vertically coordinated two units in which a copper ion is coordinated to four carboxyl groups,
the paddle-wheel structure is connected by isophthalic acid derivatives to form a Kagome structure constituted by six-membered rings and three-membered rings, and
the Kagome structure has a stacked crystal structure.

13. The porous polymer metal complex according to claim 12,
wherein the branched alkyl group is a functional group selected from the group consisting of an isopropyl group, and an isobutyl group, and
the branched alkoxy group is a functional group selected from the group consisting of an isopropyloxy group, a tert-butyloxy group, and an isobutyloxy group.

14. A porous polymer metal complex expressed by Formula (34):

$$[CuX]_n \qquad (34)$$

wherein, in the Formula, X represents two or more types of isophthalic acids selected from isophthalic acid ions and isophthalic acid ions having a substituent at position 5, an amount of isophthalic acid ions having a branched alkyl group or a branched alkoxy group at position 5 is 5 mol % or more with respect to the total number of moles of X, and n represents an assembly number of constituent units expressed by CuX and is not particularly limited.

15. The porous polymer metal complex according to claim 14,
wherein X in Formula (34) represents two or more types of ions selected from the group consisting of isophthalic acid ions, isophthalic acid ions having an alkyl group at position 5, isophthalic acid ions having an alkoxy group at position 5, isophthalic acid ions having a unsubstituted or substituted amino group at position 5.

16. A porous polymer metal complex expressed by Formula (41):

$$[CuX]_n \qquad (41)$$

wherein, in the Formula, X represents a functional group selected from the group consisting of isophthalic acid ions in which position 5 is substituted by a perfluoroalkyl group containing 3 to 21 fluorine atoms and isophthalic acid ions in which position 5 is substituted by a perfluoroalkoxy group selected from O-n-$C_3F_7$, O-n-$C_4F_9$,—O-n-$C_5F_{11}$, O-n-$C_6F_{13}$, O-n-$C_7F_{15}$, and O-n-$C_8F_{17}$, and n represents an assembly number of constituent units expressed by CuX and is not particularly limited,
wherein the porous polymer metal complex has a paddle-wheel structure having vertically coordinated two units in which a copper ion is coordinated to four carboxyl groups,
the paddle-wheel structure is connected by isophthalic acid derivatives to form a Kagome structure constituted by six-membered rings and three-membered rings, and
the Kagome structure has a stacked crystal structure.

17. A porous polymer metal complex expressed by Formula (44):

$$[CuX]_n \qquad (44)$$

wherein, in the Formula, X includes at least one type of non-fluorinated isophthalic acid ions selected from the group consisting of isophthalic acid ions in which position 5 is substituted by an alkyl group having 1 to 10 carbon atoms, isophthalic acid ions in which position 5 is substituted by an alkoxy group having 1 to 10 carbon atoms, and isophthalic acid ions, and at least one type of fluorinated isophthalic acid ions selected from isophthalic acid ions in which position 5 is substituted by a perfluoroalkyl group containing 3 to 21 fluorine atoms and isophthalic acid ions in which position 5 is substituted by a perfluoroalkoxy group containing 3 to 21 fluorine atoms, an amount of the fluorinated isophthalic acid ions is 5 mol % or more with respect to the total number of moles of X, and n represents an assembly number of constituent units expressed by CuX and is not particularly limited.

18. The porous polymer metal complex according to claim 16,
   wherein the perfluoroalkyl group is selected from $n\text{-}C_3F_7$, $n\text{-}C_4F_9$, $n\text{-}C_5F_{11}$, $n\text{-}C_6F_{13}$, $\text{-}n\text{-}C_7F_{15}$, and $n\text{-}C_8F_{16}$.

19. A gas adsorbent comprising:
   the polymer metal complex according to claim 1.

20. A gas separation device comprising the gas adsorbent to claim 19.

21. A gas storage device comprising the gas adsorbent according to claim 19.

* * * * *

UNITED STATES PATENT AND TRADEMARK OFFICE
CERTIFICATE OF CORRECTION

| | | |
|---|---|---|
| PATENT NO. | : 9,630,164 B2 | Page 1 of 1 |
| APPLICATION NO. | : 14/440014 | |
| DATED | : April 25, 2017 | |
| INVENTOR(S) | : Kajiro et al. | |

It is certified that error appears in the above-identified patent and that said Letters Patent is hereby corrected as shown below:

On the Title Page

At item (73), Assignee, change:
"(73) Assignee: NIPPON STEEL & SUMITOMO METAL CORPORATION, Tokyo (JP)"
To:
--(73) Assignees: NIPPON STEEL & SUMITOMO METAL CORPORATION, Tokyo (JP); KYOTO UNIVERSITY, Kyoto (JP)--.

Signed and Sealed this
Tenth Day of July, 2018

Andrei Iancu
*Director of the United States Patent and Trademark Office*